United States Patent
Fujii et al.

(10) Patent No.: US 8,003,350 B2
(45) Date of Patent: Aug. 23, 2011

(54) MUTANT FIREFLY LUCIFERASE, GENE, RECOMBINANT VECTOR, TRANSFORMANT, AND METHOD FOR PRODUCTION OF MUTANT FIREFLY LUCIFERASE

(75) Inventors: Hiroya Fujii, Tochigi (JP); Kenichi Noda, Ibaraki (JP)

(73) Assignee: Bioenex Inc., Hiroshima (JP)

( * ) Notice: Subject to any disclaimer, the term of this patent is extended or adjusted under 35 U.S.C. 154(b) by 446 days.

(21) Appl. No.: 11/991,455

(22) PCT Filed: Sep. 6, 2006

(86) PCT No.: PCT/JP2006/317667
§ 371 (c)(1), (2), (4) Date: Oct. 1, 2008

(87) PCT Pub. No.: WO2007/029747
PCT Pub. Date: Mar. 15, 2007

(65) Prior Publication Data
US 2009/0305353 A1    Dec. 10, 2009

(30) Foreign Application Priority Data

Sep. 6, 2005 (JP) ................................. 2005-258337
Mar. 24, 2006 (JP) ................................. 2006-083506

(51) Int. Cl.
*C12P 21/02* (2006.01)
*C07H 21/04* (2006.01)

(52) U.S. Cl. ...................................... 435/69.5; 536/23.2

(58) Field of Classification Search ........................ None
See application file for complete search history.

(56) References Cited

U.S. PATENT DOCUMENTS
6,812,012 B1    11/2004   Hattori et al.
(Continued)

FOREIGN PATENT DOCUMENTS
JP         3-285683         12/1991
(Continued)

OTHER PUBLICATIONS

Guo et al., Protein tolerance to random amino acid change, 2004, Proc. Natl. Acad. Sci. USA 101: 9205-9210.*

(Continued)

*Primary Examiner* — Alexander Kim
(74) *Attorney, Agent, or Firm* — Wenderoth, Lind & Ponack, L.L.P.

(57) ABSTRACT

The present invention provides a mutant firefly luciferase consisting of a mutant amino acid sequence derived from the amino acid sequence of a wild-type firefly luciferase by at least substitution (a), (b), or (c) below and having luminescence intensity higher than that of the wild-type firefly luciferase. According to the present invention, a mutant firefly luciferase with increased luminescence intensity compared with that of wild-type firefly luciferases is provided, regarding which (a) through (c) are as follows:

(a) substitution of at least one of the amino acids at positions equivalent to positions 419 to 428 in the amino acid sequence of North American firefly luciferase with a non-polar amino acid having a molecular weight that is the same as or higher than that of the amino acid to be substituted;

(b) substitution of at least one of the amino acids at positions equivalent to positions 435 to 441 in the amino acid sequence of North American firefly luciferase with an amino acid that has a molecular weight lower than that of the amino acid to be substituted and is selected from among glycine, alanine, and serine; and (c) substitution of at least one of the amino acids at positions equivalent to positions 523 to 532 in the amino acid sequence of North American firefly luciferase with a positively-charged amino acid that has an isoelectric point higher than that of the amino acid to be substituted.

1 Claim, 1 Drawing Sheet

U.S. PATENT DOCUMENTS

2004/0235077 A1    11/2004    Hattori et al.

FOREIGN PATENT DOCUMENTS

| | | |
|---|---|---|
| JP | 2666561 | 6/1997 |
| JP | 11-239493 | 9/1999 |
| JP | 2003-518912 | 6/2003 |
| WO | 00/24878 | 5/2000 |

OTHER PUBLICATIONS

Lazar et al., Transforming Growth Factor α: Mutation of Aspartic Acid 47 and Leucine 48 Results in Different Biological Activity, 1988, Mol. Cell. Biol. 8:1247-1252.*

Hill et al., Functional Analysis of conserved Histidines in ADP-Glucose Pyrophosphorylase from *Escherichia coli*, 1998, Biochem. Biophys. Res. Comm. 244:573-577.*

White et al., Improved thermostability of the North American firefly luciferase: saturation mutagenesis at position 354., Biochem. J., 1996, vol. 319, pp. 343-350.*

Amino Acid Structure (last viewed on Nov. 11, 2010).*

B. R. Branchini et al., "The Role of Lysine 529, A Conserved Residue of the Acyl-Adenylate-Forming Enzyme Superfamily, in Firefly Luciferase", Biochemistry, vol. 39, No. 18, pp. 5433-5440, 2000.

B. R. Branchini et al., "Site-Directed Mutagenesis of Firefly Luciferase Active Site Amino Acids: A Proposed Model for Bioluminescence Color", Biochemistry, vol. 38, No. 40, pp. 13223-13230, 1999.

B. R. Branchini et al., "Mutagenesis Evidence that the Partial Reactions of Firefly Bioluminescence are Catalyzed by Different Conformations of the Luciferase C-Terminal Domain", Biochemistry, vol. 44, No. 5, pp. 1385-1393, 2005.

K. Ayabe et al., "The Role of Firefly Luciferase C-Terminal Domain in Efficient Coupling of Adenylation and Oxidative Steps", FEBS Letters, vol. 579, pp. 4389-4394, 2005.

J. P. Waud et al., "Engineering the C-Terminus of Firefly Luciferase as an Indicator of Covalent Modification of Proteins", Biochimica et Biophysica Acta, vol. 1292, pp. 89-98, 1996.

* cited by examiner

MUTANT FIREFLY LUCIFERASE, GENE, RECOMBINANT VECTOR, TRANSFORMANT, AND METHOD FOR PRODUCTION OF MUTANT FIREFLY LUCIFERASE

This application is a U.S. national stage of International Application No. PCT/JP2006/317667 filed Sep. 6, 2006.

TECHNICAL FIELD

The present invention relates to a mutant firefly luciferase, a gene, a recombinant vector, a transformant, and a method for producing such a mutant firefly luciferase.

BACKGROUND ART

Firefly luciferases are enzymes that catalyze the oxidation of firefly luciferins in the presence of adenosine triphosphate (ATP), magnesium ion, and oxygen, so as to bring about light emissions from the luciferins. Thus, the firefly luciferases are broadly used for detection of ATP for the purpose of detecting bacteria and the like in food and drink.

To enhance the availability of such firefly luciferases for detection of ATP, various mutant firefly luciferases have been prepared thus far. As such mutant firefly luciferases, firefly luciferases with improved thermostability (for example, see JP Patent No. 3048466; JP Patent Publication (Kokai) No. 2000-197487 A; JP Patent Publication (Kohyo) No. 9-510610 A (1997); and JP Patent Publication (Kohyo) No. 2003-518912 A), firefly luciferases with improved substrate affinity (for example, see International Publication WO 99/02697 Pamphlet; JP Patent Publication (Kohyo) No. 10-512750 A (1998); and JP Patent Publication (Kohyo) No. 2001-518799 A), firefly luciferases with altered luminescence wavelengths (for example, see JP Patent No. 2666561 and JP Patent Publication (Kohyo) No. 2003-512071 A), firefly luciferases with improved luminescence continuity (for example, see JP Patent Publication (Kokai) No. 2000-197484 A), firefly luciferases with resistance to surfactants (for example, see JP Patent Publication (Kokai) No. 11-239493 A (1999)), and the like are known.

DISCLOSURE OF THE INVENTION

Object to be Achieved by the Invention

A mutant firefly luciferase with increased luminescence intensity compared with those of wild-type firefly luciferases has not yet conventionally been known. If such mutant firefly luciferase is provided, detection of trace amounts of ATP will be possible. Furthermore, such mutant firefly luciferase is also useful for detection of bacteria and the like in food and drink.

Therefore, an object of the present invention is to provide a mutant firefly luciferase with increased luminescence intensity compared with those of wild-type firefly luciferases.

Means for Achieving the Object

As a result of intensive studies to achieve the above object, the present inventors have discovered that luminescence intensity is increased by substituting amino acids at specific positions in the amino acid sequence of a wild-type firefly luciferase with specific different amino acids. Thus, the present inventors have completed the present invention.

Specifically, the present invention provides a mutant firefly luciferase consisting of a mutant amino acid sequence derived from the amino acid sequence of a wild-type firefly luciferase by at least substitution (a), (b), or (c) below and having luminescence intensity higher than that of the wild-type firefly luciferase.

(a) Substitution of at least one of the amino acids at positions equivalent to positions 419 to 428 in the amino acid sequence of North American firefly luciferase with a nonpolar amino acid having a molecular weight that is the same as or higher than that of the amino acid to be substituted.

(b) Substitution of at least one of the amino acids at positions equivalent to positions 435 to 441 in the amino acid sequence of North American firefly luciferase with an amino acid that has a molecular weight lower than that of the amino acid to be substituted and is selected from among glycine, alanine, and serine.

(c) Substitution of at least one of the amino acids at positions equivalent to positions 523 to 532 in the amino acid sequence of North American firefly luciferase with a positively-charged amino acid that has an isoelectric point higher than that of the amino acid to be substituted.

In the description, "North American firefly luciferase" means wild-type North American firefly (*Photinus pyralis*) luciferase, unless otherwise specified. Furthermore, for example, "Heike firefly luciferase" and "Genji firefly luciferase" mean wild-type Heike firefly (*Luciola lateralis*) luciferase and wild-type Genji firefly (*Luciola cruciata*) luciferase, respectively, unless otherwise specified.

Furthermore, "luminescence intensity" of firefly luciferase means, unless otherwise specified, peak luminescence intensity when the firefly luciferase is caused to react with firefly luciferin in the presence of ATP, a divalent metal ion, and oxygen. In addition, it can be concluded that the larger the luminescence intensity, the stronger the firefly luciferase activity of a firefly luciferase.

Furthermore, in the amino acid sequence of a wild-type firefly luciferase, "positions equivalent to positions 419 to 428 in the amino acid sequence of North American firefly luciferase," "positions equivalent to positions 435 to 441 in the amino acid sequence of North American firefly luciferase," and "positions equivalent to positions 523 to 532 in the amino acid sequence of North American firefly luciferase" correspond to: when the wild-type firefly luciferase is North American firefly luciferase, positions 419 to 428, 435 to 441, and 523 to 532, respectively, in the amino acid sequence of the wild-type firefly luciferase. When the wild-type firefly luciferase is not North American firefly luciferase, such positions in the amino acid sequence of the wild-type firefly luciferase correspond to positions 419 to 428, 435 to 441, and 523 to 532, respectively, in the amino acid sequence of North American firefly luciferase when the wild-type firefly luciferase and North American firefly luciferase are subjected to amino acid sequence alignment so as to maximize the degree of overlap. In addition, the amino acid sequence of North American firefly luciferase is as shown in SEQ ID NO: 1.

Furthermore, a "nonpolar amino acid" means an amino acid having a nonpolar group in its side chain. A "positively-charged amino acid" means an amino acid that is positively charged at a physiological pH (pH 7.4).

When a luciferin-luciferase reaction is performed using the above mutant firefly luciferase, the luminescence intensity can be increased compared with cases in which wild-type firefly luciferases are used. This is because the reaction rate of the luciferin-luciferase reaction is increased due to the above amino acid substitution.

Preferable examples of the mutant amino acid sequences of the above mutant fireflyluciferases are derived from the amino acid sequence of a wild-type firefly luciferase by at least substitutions (a) and (b) above, (a) and (c) above, or (a), (b), and (c) above. When a luciferin-luciferase reaction is performed using a mutant firefly luciferase consisting of such a mutant amino acid sequence, the luminescence intensity can further be increased compared with a case in which each substitution takes place independently. This is because the reaction rate of the luciferin-luciferase reaction is further increased through a combination of substitutions (a) and (b) above, substitutions (a) and (c) above, or substitutions (a), (b), and (c) above, compared with a case in which each substitution takes place independently. In addition, the mutant amino acid sequence may be a mutant amino acid sequence derived from the amino acid sequence of a wild-type firefly luciferase by at least substitutions (b) and (c) above.

Furthermore, a preferable example of the mutant amino acid sequences of the above mutant firefly luciferases has 60% or more homology with the amino acid sequence of North American firefly luciferase. If such homology with the amino acid sequence of North American firefly luciferase is less than 60%, the resulting luminescence intensity tends to be lower compared with cases of 60% or higher homology.

The above mutant firefly luciferase can be obtained by culturing a transformant having a recombinant vector that contains a gene encoding the mutant firefly luciferase and then collecting the mutant firefly luciferase from the thus obtained culture.

Specifically, the present invention further provides a gene encoding the above mutant firefly luciferase, a recombinant vector containing such gene, and a transformant having the recombinant vector. Moreover, the present invention further provides a method for producing a mutant firefly luciferase comprising the steps of culturing the above transformant to obtain a culture and collecting the above mutant firefly luciferase from the culture.

With the use of the above gene, the above recombinant vector, the above transformant, and the above method for producing a mutant firefly luciferase, the above mutant firefly luciferase can be efficiently produced.

Moreover, reporter assay can be performed with higher sensitivity with the use of the above gene as a reporter gene, compared with cases of using wild-type firefly luciferase genes. Such reporter assay is made possible with the use of the above recombinant vector.

Effect of the Invention

According to the present invention, a mutant firefly luciferase with increased luminescence intensity compared with that of a wild-type firefly luciferase is provided.

EXPLANATION OF LETTERS OR NUMERALS

Figure 1:
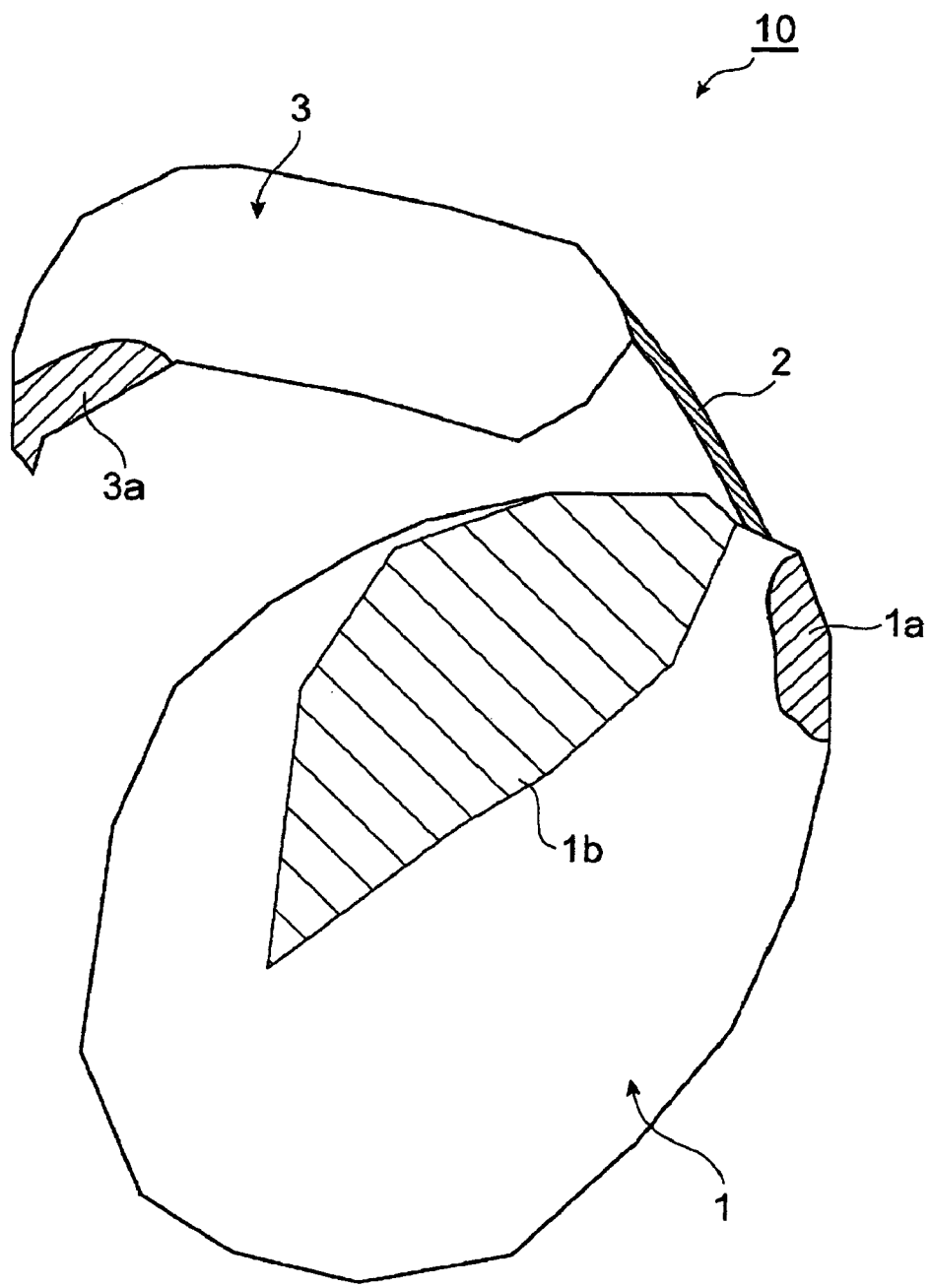
FIG. 1 schematically shows the conformation of a firefly luciferase.

10 . . . firefly luciferase, 1 . . . N-terminal domain, 1a . . . junction, 1b . . . active site, 2 . . . connection, and 3 . . . C-terminal domain, 3a . . . tip.

BEST MODE OF CARRYING OUT THE INVENTION

Hereinafter, the preferred embodiments of the present invention will be explained.

(Mutant Firefly Luciferase)

The mutant firefly luciferase of the present invention consists of a mutant amino acid sequence derived from the amino acid sequence of a wild-type firefly luciferase by at least substitution (a), (b), or (c) below and
has luminescence intensity higher than that of the wild-type firefly luciferase.

(a) Substitution of at least one amino acid (amino acid A) among amino acids at positions equivalent to positions 419 to 428 in the amino acid sequence of North American firefly luciferase with a nonpolar amino acid having a molecular weight that is the same as or higher than that of the amino acid A.

(b) Substitution of at least one amino acid (amino acid B) among amino acids at positions equivalent to positions 435 to 441 in the amino acid sequence of North American firefly luciferase with an amino acid that has a molecular weight lower than that of the amino acid B and is selected from among glycine, alanine, and serine.

(c) Substitution of at least one amino acid (amino acid C) among amino acids at positions equivalent to positions 523 to 532 in the amino acid sequence of North American firefly luciferase with a positively-charged amino acid that has an isoelectric point higher than that of the amino acid C.

Examples of wild-type firefly luciferases include North American firefly (*Photinus pyralis*) luciferase, Heike firefly (*Luciola lateralis*) luciferase, Genji firefly (*Luciola cruciata*) luciferase, East European firefly (*Luciola mingrelica*) luciferase, and glow worm (*Lampyris noctiluca*) luciferase. In addition, the amino acid sequences of various wild-type firefly luciferases can be searched using a database (e.g., EMBL-EBI Database (www.ebi.ac.uk/queries/)).

When a wild-type firefly luciferase is not North American firefly luciferase, "positions equivalent to positions 419 to 428 in the amino acid sequence of North American firefly luciferase," "positions equivalent to positions 435 to 441 in the amino acid sequence of North American firefly luciferase," and "positions equivalent to positions 523 to 532 in the amino acid sequence of North American firefly luciferase" in the amino acid sequence of the wild-type firefly luciferase can be determined via analysis of amino acid sequence homology between the wild-type firefly luciferase and North American firefly luciferase using software for analysis of amino acid sequence homology (e.g., Micro Genie (produced by Beckman Coulter, Inc.)) or the like. In addition, the amino acid sequence of North American firefly luciferase is as shown in SEQ ID NO: 1.

For example, "positions equivalent to positions 419 to 428 in the amino acid sequence of North American firefly luciferase," "positions equivalent to positions 435 to 441 in the amino acid sequence of North American firefly luciferase," and "positions equivalent to positions 523 to 532 in the amino acid sequence of North American firefly luciferase" in the amino acid sequence of the wild-type firefly luciferase are: when the wild-type firefly luciferase is Heike firefly luciferase or Genji firefly luciferase, positions 421 to 430, 437 to 443, and 525 to 534, respectively, in the amino acid sequence of the wild-type firefly luciferase. In addition, the amino acid sequence of Heike firefly luciferase and that of Genji firefly luciferase are as shown in SEQ ID NOS: 2 and 3, respectively.

Examples of a nonpolar amino acid include alanine, proline, valine, leucine, isoleucine, methionine, phenylalanine, and tryptophan. In view of the height of hydrophobicity, leucine, isoleucine, methionine, phenylalanine, and tryptophan are preferred and leucine and methionine are more preferred. Examples of positively-charged amino acid include arginine, lysine, and histidine. In view of positive charge strength, arginine and lysine are preferred and arginine is more preferred.

FIG. 1 schematically shows the conformation of a firefly luciferase. As shown in FIG. 1, firefly luciferase 10 consists of N-terminal domain 1, C-terminal domain 3, and movable connection 2 that connects them. Moreover, active site 1b of the enzyme is present in N-terminal domain 1, facing to C-terminal domain 3.

Junction 1a, where N-terminal domain 1 and connection 2 join, corresponds to a sequence portion composed of amino acids at positions equivalent to positions 419 to 428 in the amino acid sequence of North American firefly luciferase. Connection 2 corresponds to a sequence portion composed of amino acids at positions equivalent to positions 435 to 441 in the amino acid sequence of North American firefly luciferase. Tip 3a in C-terminal domain 3 corresponds to a sequence portion composed of amino acids at positions equivalent to positions 523 to 532 in the amino acid sequence of North American firefly luciferase. Such relationships between amino acid sequences of firefly luciferases and conformations can be confirmed using conformational analysis software (e.g., Bio Package (produced by Molsoft)).

When a luciferin-luciferase reaction is performed using the above mutant firefly luciferase, luminescence intensity can be increased compared with a case of using a wild-type firefly luciferase. This is because the reaction rate of the luciferin-luciferase reaction increases as a result of substitution of the above amino acids.

For a reaction of a firefly luciferase with firefly luciferin, N-terminal domain 1 should be located close to C-terminal domain 3. In a mutant firefly luciferase in which substitution (a) above has taken place, it is inferred that substitution of any one of amino acids composing junction 1a in N-terminal domain 1 with a nonpolar amino acid having a molecular weight that is the same as or higher than that of the original amino acid to be substituted results in more enhanced hydrophobicity of junction 1a and enhanced accessibility of N-terminal domain 1 to C-terminal domain 3 compared with a wild-type firefly luciferase. Furthermore, in a mutant firefly luciferase in which substitution (b) above has taken place, it is inferred that substitution of any one of amino acids composing movable connection 2 with an amino acid that has a molecular weight lower than that of the original amino acid to be substituted and is selected from among glycine, alanine, and serine results in a greater degree of movability of connection 2 compared with that of a wild-type firefly luciferase and enhanced accessibility of N-terminal domain 1 to C-terminal domain 3.

For a reaction of a firefly luciferase with firefly luciferin, the firefly luciferin and ATP should be incorporated into active site 1b of the firefly luciferase. In a mutant firefly luciferase in which substitution (c) above has taken place, it is inferred that substitution of any one of amino acids composing tip 3a of C-terminal domain 3 with a positively-charged amino acid having an isoelectric point higher than that of the original amino acid to be substituted results in more positively charged tip 3a and facilitated incorporation of negatively charged firefly luciferin and ATP into active site 1b of the enzyme.

A preferable example of the mutant amino acid sequences of the above mutant firefly luciferases is the amino acid sequence of a wild-type firefly luciferase in which at least substitutions (a) and (b) above, substitutions (a) and (c) above, or substitutions (a), (b), and (c) above have taken place. When a luciferin-luciferase reaction is performed using a mutant firefly luciferase consisting of such a mutant amino acid sequence, luminescence intensity can be further increased compared with a case in which each substitution has taken place independently. This is because a combination of substitutions (a) and (b) above, a combination of substitutions (a) and (c) above, or a combination of substitutions (a), (b), and (c) above results in further increased reaction rate of a luciferin-luciferase reaction compared with a case in which each substitution has taken place independently. In addition, an example of such mutant amino acid sequence may be the amino acid sequence of a wild-type firefly luciferase, in which at least substitutions (b) and (c) above have taken place.

A preferable example of the mutant amino acid sequences of the above mutant firefly luciferases has 60% or more homology with the amino acid sequence of North American firefly luciferase in view of luminescence intensity. The homology is more preferably 65% or more, further preferably 70% or more, further preferably 80% or more, and further preferably 90% or more.

An example of the mutant amino acid sequences of the above mutant firefly luciferases may be the amino acid sequence of a wild-type firefly luciferase, in which a mutation(s) other than substitutions (a), (b), and (c) above (amino acid substitution, deletion, insertion, or addition) has further taken place. For example, a mutation that enhances thermostability (e.g., see JP Patent No. 3048466; JP Patent Publication (Kokai) No. 2000-197487 A; JP Patent Publication (Kohyo) No. 9-510610 A (1997); and JP Patent Publication (Kohyo) No. 2003-518912 A), a mutation that enhances substrate affinity (e.g., see International Publication WO 99/02697 Pamphlet; JP Patent Publication (Kohyo) No. 10-512750 A (1998); and JP Patent Publication (Kohyo) No. 2001-518799 A), a mutation that alters luminescence wavelengths (e.g., see JP Patent No. 2666561; and JP Patent Publication (Kohyo) No. 2003-512071 A), a mutation that enhances continuousness of luminescence (e.g., see JP Patent Publication (Kokai) No. 2000-197484 A), or a mutation that imparts surfactant resistance (e.g., see JP Patent Publication (Kokai) No. 11-239493 A (1999)) may further be introduced.

Among mutant firefly luciferases each consisting of a mutant amino acid sequence derived from the amino acid sequence of a wild-type firefly luciferase by at least substitution (a), (b), or (c) above, the mutant firefly luciferase of the present invention has luminescence intensity higher than that of the wild-type firefly luciferase. Whether or not a mutant firefly luciferase consisting of the above mutant amino acid sequence is the mutant firefly luciferase of the present invention can be confirmed by reacting the mutant firefly luciferase with firefly luciferin in the presence of ATP, a divalent metal ion (e.g., a magnesium ion), and oxygen and then measuring luminescence intensity. If the measured luminescence intensity is increased compared with that of the above wild-type firefly luciferase, it can be concluded that the luciferase is the mutant firefly luciferase of the present invention. Furthermore, examples of firefly luciferin include luciferin derived from North American firefly (*Photinus pyralis*), luciferin derived from Heike firefly (*Luciola lateralis*), luciferin derived from Genji firefly (*Luciola cruciata*), luciferin derived from East European firefly (*Luciola mingrelica*), and luciferin derived from glow worm (*Lampyris noctiluca*).

Mutant firefly luciferases (1) to (7) below are preferred embodiments of the mutant firefly luciferase of the present invention:

(1) a mutant firefly luciferase, consisting of an amino acid sequence derived from the amino acid sequence of a wild-type firefly luciferase by substitution of an amino acid at least one of the positions equivalent to positions 419 to 428 in the amino acid sequence of North American firefly luciferase with a nonpolar amino acid having a molecular weight that is the same as or higher than that of the amino acid;

(2) a mutant firefly luciferase, consisting of an amino acid sequence derived from the amino acid sequence of a wild-type firefly luciferase by substitution of an amino acid at least one of the positions equivalent to positions 435 to 441 in the amino acid sequence of North American firefly luciferase with an amino acid that has a molecular weight lower than that of the amino acid and is selected from among glycine, alanine, and serine;

(3) a mutant firefly luciferase, consisting of an amino acid sequence derived from the amino acid sequence of a wild-type firefly luciferase by substitution of an amino acid at least one of the positions equivalent to positions 523 to 532 in the amino acid sequence of North American firefly luciferase with a positively-charged amino acid having an isoelectric point higher than that of the amino acid;

(4) a mutant firefly luciferase, consisting of an amino acid sequence derived from the amino acid sequence of a wild-type firefly luciferase by substitution of a first amino acid at least one of the positions equivalent to positions 419 to 428 in the amino acid sequence of North American firefly luciferase with a nonpolar amino acid having a molecular weight that is the same as or higher than that of the first amino acid and substitution of a second amino acid at least one of the positions equivalent to positions 435 to 441 in the amino acid sequence of North American firefly luciferase with an amino acid that has a molecular weight lower than that of the second amino acid and is selected from among glycine, alanine, and serine;

(5) a mutant firefly luciferase, consisting of an amino acid sequence derived from the amino acid sequence of a wild-type firefly luciferase by substitution of a first amino acid at least one of the positions equivalent to positions 419 to 428 in the amino acid sequence of North American firefly luciferase with a nonpolar amino acid having a molecular weight that is the same as or higher than that of the first amino acid and by substitution of a second amino acid at least one of the positions equivalent to positions 523 to 532 in the amino acid sequence of North American firefly luciferase with a positively-charged amino acid having an isoelectric point higher than that of the second amino acid;

(6) a mutant firefly luciferase, consisting of an amino acid sequence derived from the amino acid sequence of a wild-type firefly luciferase by substitution of a first amino acid at least one of the positions equivalent to positions 435 to 441 in the amino acid sequence of North American firefly luciferase with an amino acid that has a molecular weight lower than that of the first amino acid and is selected from among glycine, alanine, and serine and by substitution of a second amino acid at least one of the positions equivalent to positions 523 to 532 in the amino acid sequence of North American firefly luciferase with a positively-charged amino acid having an isoelectric point higher than that of the second amino acid; and (7) a mutant firefly luciferase, consisting of an amino acid sequence derived from the amino acid sequence of a wild-type firefly luciferase by substitution of a first amino acid at least one of the positions equivalent to positions 419 to 428 in the amino acid sequence of North American firefly luciferase with a nonpolar amino acid having a molecular weight that is the same as or higher than that of the first amino acid, substitution of a second amino acid at least one of the positions equivalent to positions 435 to 441 in the amino acid sequence of North American firefly luciferase with an amino acid that has a molecular weight lower than that of the second amino acid and is selected from among glycine, alanine, and serine, and substitution of a third amino acid at least one of the positions equivalent to positions 523 to 532 in the amino acid sequence of North American firefly luciferase with a positively-charged amino acid having an isoelectric point higher than that of the third amino acid.

Mutant firefly luciferase (1) above is a mutant firefly luciferase consisting of a mutant amino acid sequence derived from the amino acid sequence of a wild-type firefly luciferase by substitution (a) above. Mutant firefly luciferase (2) above is a mutant firefly luciferase consisting of a mutant amino acid sequence derived from the amino acid sequence of a wild-type firefly luciferase by substitution (b) above. Mutant firefly luciferase (3) above is a mutant firefly luciferase consisting of a mutant amino acid sequence derived from the amino acid sequence of a wild-type firefly luciferase by substitution (c) above. Mutant firefly luciferase (4) above is a mutant firefly luciferase consisting of a mutant amino acid sequence derived from the amino acid sequence of a wild-type firefly luciferase by substitutions (a) and (b). Mutant firefly luciferase (5) above is a mutant firefly luciferase consisting of a mutant amino acid sequence derived from the amino acid sequence of a wild-type firefly luciferase by substitutions (a) and (c) above. Mutant firefly luciferase (6) above is a mutant firefly luciferase consisting of a mutant amino acid sequence derived from the amino acid sequence of a wild-type firefly luciferase by substitutions (b) and (c) above. Mutant firefly luciferase (7) above is a mutant firefly luciferase consisting of a mutant amino acid sequence derived from the amino acid sequence of a wild-type firefly luciferase by substitutions (a), (b), and (c) above.

The mutant firefly luciferases (1) to (7) above have sufficiently high luminescence intensities compared with those of original wild-type firefly luciferases. In particular, the mutant firefly luciferases (4), (5), and (7) above have significantly higher luminescence intensities than those of original wild-type firefly luciferases. For all of the mutant firefly luciferases (1) to (7) above, North American firefly luciferase is preferable as an example of such original wild-type firefly luciferases in view of luminescence intensity.

A further preferable embodiment of the mutant firefly luciferase of the present invention is, for example, a mutant firefly luciferase consisting of an amino acid sequence derived from the amino acid sequence of North American firefly luciferase by substitution of a first amino acid at least one of the positions 419 to 428 with a nonpolar amino acid having a molecular weight that is the same as or higher than that of the first amino acid, substitution of a second amino acid at least one of the positions 523 to 532 with a positively-charged amino acid having an isoelectric point higher than that of the second amino acid, substitution of isoleucine at position 47 with threonine, substitution of asparagine at position 50 with serine, substitution of methionine at position 59 with threonine, and substitution of threonine at position 252 with serine. The resulting mutant firefly luciferase has further higher luminescence intensity than those of the mutant firefly luciferases (1) to (7) above.

(Gene)

The gene of the present invention is a mutant firefly luciferase gene encoding the mutant firefly luciferase of the present invention. Here, "gene" comprises DNA or RNA.

The above mutant firefly luciferase gene can be obtained by altering a wild-type firefly luciferase gene. Genetic modification can be performed by methods known by persons killed in the art, such as site-specific mutagenesis, random mutagenesis, or organic synthesis.

Site-specific mutagenesis or random mutagenesis is performed using a wild-type firefly luciferase gene or a recombinant vector containing the gene as a template. A wild-type firefly luciferase gene or a recombinant vector containing the gene can be prepared according to a method known by persons skilled in the art (e.g., a method disclosed in "*Idenshi Ko-gaku Jikken Note* (Genetic Engineering Experimental Note) (YODOSHA CO., LTD)," JP Patent Publication (Kokai) No. 1-51086 A (1989), or JP Patent No. 3048466). Furthermore, commercial products thereof may also be used herein.

Site-specific mutagenesis can be performed by a method known by persons skilled in the art, such as a method that involves synthesis using a selection primer, a mutagenesis primer, and T4 DNA polymerase. Suppose there is a case in which site-specific mutagenesis is performed using a recombinant vector that contains a wild-type firefly luciferase gene as a template, a selection primer, and a mutagenesis primer. For example, when a DNA fragment containing a sequence that differs from the restriction enzyme recognition sequence existing within the recombinant vector by a single nucleotide is used as a selection primer in such a case, the restriction enzyme recognition sequence remains intact in a recombinant vector in which no mutation has been introduced. Hence, such a recombinant vector in which no mutation has been introduced can be selected and removed by cleavage treatment using a restriction enzyme corresponding thereto.

Random mutagenesis can be performed by a method known by persons skilled in the art, such as a method that involves lowering fidelity by the addition of manganese and dGTP and then performing polymerase chain reaction (PCR), a method that involves causing a drug (e.g., hydroxylamine and N-methyl-N'-nitro-N-nitrosoguanidine) to come into contact, and a method that involves UV irradiation. When random mutagenesis is performed, a target mutant firefly luciferase gene or a recombinant vector containing the gene can be selected through determination of the nucleotide sequence of a gene into which mutation has been introduced.

The nucleotide sequence of a gene into which mutation has been introduced can be determined by a method known by persons skilled in the art, such as a dideoxy chain termination method. In addition, a database (e.g., EMBL Nucleotide Sequence Database (www.ebi.ac.uk/embl/)) can be searched for the nucleotide sequences of various wild-type firefly luciferase genes (cDNAs).

(Recombinant Vector)

The recombinant vector of the present invention is a recombinant vector containing the mutant firefly luciferase gene of the present invention.

The above recombinant vector can be obtained according to a method known by persons skilled in the art, which involves inserting the mutant firefly luciferase gene into a vector (e.g., a plasmid and a bacteriophage) replicable within host cells. Such insertion of the mutant firefly luciferase gene into a vector can be performed by digesting a DNA fragment (prepared by addition of an appropriate restriction enzyme recognition sequence to the relevant mutant firefly luciferase gene) using the corresponding restriction enzyme and then ligating the thus obtained gene fragment to the vector via its insertion to the corresponding restriction enzyme recognition sequence or the multi-cloning site in the vector.

The above recombinant vector can also be obtained, as described above, by introducing mutation into a recombinant vector containing a wild-type firefly luciferase gene.

Examples of a plasmid include plasmids derived from *Escherichia coli* (e.g., pET28a(+), pGL2, pBR322, pUC18, pTrcHis, and pBlueBacHis), plasmids derived from *Bacillus subtilis* (e.g., pUB110 and pTP5), and plasmids derived from yeast (e.g., YEp13, YEp24, YCp50, and pYE52). Examples of a bacteriophage include λphage and the like.

For expression of the above mutant firefly luciferase gene in host cells, an appropriate promoter capable of functioning within host cells should be arranged upstream of the mutant firefly luciferase gene. Moreover, according to need, an enhancer, a terminator, a splicing signal, a polyA addition signal, a ribosome binding sequence (SD sequence), and the like can be arranged.

Reporter assay can be performed with sufficiently high sensitivity through the use of the above mutant firefly luciferase gene as a reporter gene. Such reporter assay becomes possible by the use of the above recombinant vector containing the above mutant firefly luciferase gene.

(Transformant)

The transformant of the present invention is a transformant having the recombinant vector of the present invention.

The above transformant can be obtained according to a method known by persons skilled in the art, which involves introducing the above recombinant vector into host cells. Introduction of the above recombinant vector into host cells can be performed by a method known by persons skilled in the art, such as a calcium chloride method, an electroporation method, a polyethylene glycol method, and a particle gun method.

Examples of host cells include bacteria (e.g., *Escherichia coli* and *Bacillus subtilis*), yeast (e.g., *Saccharomyces cerevisiae*), animal cells (e.g, COS cells and CHO cells), and insect cells (e.g., Sf19 and Sf21). *Escherichia coli* is preferable because of its rapid growth and the ease in which it can be handled.

When *Escherichia coli* is used as a host cell, examples of a promoter that is arranged within the above recombinant vector include a trp promoter, a lac promoter, a T7 promoter, a PL promoter, and a PR promoter.

(Method for Producing Mutant Firefly Luciferase)

The method for producing a mutant firefly luciferase of the present invention comprises the steps of culturing the transformant of the present invention so as to obtain a culture and collecting the mutant firefly luciferase of the present invention from the culture. The mutant firefly luciferase of the present invention can be obtained by the production method.

The culturing step is a step by which a culture is obtained by culturing the transformant of the present invention. Here, a "culture" may be any of culture supernatants, cultured cells, and disrupted cells. The above transformant can be cultured by a method known by persons skilled in the art. The medium to be used for culturing the above transformant may be, when host cells are microorganisms such as *Escherichia coli* or yeast, any natural medium or synthetic medium or any liquid medium or solid medium, as long as such medium contains a carbon source assimilable by such microorganisms (e.g., glucose, sucrose, and lactose), a nitrogen source (e.g., peptone, a meat extract, and a yeast extract), inorganic salts (e.g., phosphate, carbonate, and sulfate), and the like and enables efficient culturing of host cells, for example. Which one of shake culture, agitation culture, static culture, and the like is performed and other culture conditions (e.g., the temperature for culturing, the pH for medium, and the time for culturing) can be adequately determined based on the host cells, medium, and the like to be employed. For example, when a host cell is *Escherichia coli*, the culture temperature generally ranges from 30° C. to 42° C. and is preferably 37° C. The pH for the medium generally ranges from 6.4 to 8.0 and preferably ranges from 7.0 to 7.4. When the temperature for culturing is 37° C., the time for culturing generally ranges from 8 to 20 hours and preferably ranges from 12 to 16 hours in the case of preculture. The time for culturing in the case of main culture before expression induction ranges from 2 to 8 hours and preferably ranges from 2 to 4 hours. However, the optimum time for culturing is determined according to the temperature for culturing and the pH for the medium.

An expression inducer can be added to medium according to need. Examples of such expression inducer include, when the above recombinant vector contains a lac promoter, isopropyl β-thiogalactoside (IPTG) and the like and when the same contains a trp promoter, indoleacrylic acid (IAA) and the like.

When the above recombinant vector is constructed using a vector having resistance to antibiotics (e.g., kanamycin and ampicillin), the relevant antibiotic is added to medium in advance, so that resistance to the antibiotic can be used as a selection marker for the above transformant.

The collecting step is a step of collecting the mutant firefly luciferase of the present invention from a culture obtained by the culturing step. The above mutant firefly luciferase can be collected by a method known by persons skilled in the art, such as a method that involves collecting the transformant from a culture by centrifugation and then performing freezing and thawing, ultrasonic disintegration, or treatment using a lytic enzyme such as lysozyme. In addition, the thus collected mutant firefly luciferase may exist in the form of a solution.

In the above production method, preferably a purification step for purifying the above mutant firefly luciferase (crude enzyme) obtained by the collecting step is further performed after the collecting step. A crude enzyme can be purified through ammonium sulfate precipitation, SDS-PAGE, gel filtration chromatography, ion exchange chromatography, affinity chromatography, or the like independently or through adequate combination thereof.

Whether or not the mutant firefly luciferase of the present invention has been obtained can be confirmed by reacting the luciferase with firefly luciferin in the presence of ATP, a divalent metal ion (e.g., a magnesium ion), and oxygen and then measuring the luminescence intensity. If the luminescence intensity is increased compared with that of the original wild-type firefly luciferase (into which mutation has been introduced), it can be concluded that the mutant firefly luciferase of the present invention is obtained.

The gene, recombinant vector, transformant, and method for producing a mutant firefly luciferase of the present invention enable efficient production of the mutant firefly luciferase of the present invention.

EXAMPLES

Hereafter, the present invention will be described further specifically based on Examples and Comparative examples. However, the present invention is not limited by the following Examples.

Example 1

A mutant firefly luciferase consisting of an amino acid sequence derived from the amino acid sequence of North American firefly luciferase was produced as described below by substitution of isoleucine (Ile) at position 423 with leucine (Leu). Its firefly luciferase activity (luminescence intensity) was measured.

Preparation of a Recombinant Plasmid Containing a Mutant Firefly Luciferase Gene:

First, PCR was performed using a plasmid (pGL2-Basic Vector (produced by Promega Corporation)) containing a North American firefly (*Photinus pyralis*) luciferase gene (cDNA) (the nucleotide sequence thereof is as shown in SEQ ID NO: 4) as a template and DNA consisting of the nucleotide sequence: 5'-gactccatggaagacgccaaaaac-3' (SEQ ID NO: 5) containing a restriction enzyme Nco I recognition sequence and DNA consisting of the nucleotide sequence: 5'-gacactcgagcaatttggactttccgcc-3' (SEQ ID NO: 6) containing a restriction enzyme Xho I recognition sequence as primers. A solution used as a PCR reaction solution was prepared by adding each primer DNA (0.2 µM) and template DNA at 50 ng/50 µL to TITANIUM Taq DNA polymerase, dNTP Mix, and TITANIUM Taq buffer provided with a Diversify PCR Random Mutagenesis Kit (produced by Clontech). Reaction was performed by repeating 25 times a cycle consisting of "94° C. for 30 seconds, 55° C. for 30 seconds, and 72° C. for 120 seconds" using GeneAmp PCR System 2700 (produced by Applied Biosystems). Thus, a DNA fragment containing North American firefly luciferase gene was obtained. The nucleotide sequence was determined using a DTCS Quick Start Master Mix kit and electrophoresis analysis apparatus CEQ8000 (both produced by Beckman Coulter). The DNA fragment to which the 2 above types of restriction enzyme recognition sequence had been added was cleaved with Nco I and Xho I (both produced by New England Biolabs). The resultant was incorporated into a plasmid (pET-28a(+) plasmid DNA (produced by Novagen)) that had been cleaved with Nco I and Xho I in advance using a DNA Ligation Kit (produced by BioDynamics Laboratory). In addition, pET-28a(+) contained a T7 promoter and a T7 terminator. Furthermore, pET-28a(+) contained a gene encoding a histidine tag in the vicinity of the cloning site, so that the histidine tag was added to the C-terminal side of the target protein to be expressed. Moreover, pET-28a(+) had kanamycin resistance.

Next, site-specific mutagenesis was performed using the thus obtained recombinant plasmid as a template and a Transformer site-directed mutagenesis kit (produced by Clontech). A selection primer used herein was a DNA consisting of the nucleotide sequence: 5'-cacgatcatgagcacccgtgg-3' (SEQ ID NO: 7) containing a sequence differing from a restriction enzyme Fsp I recognition sequence in pET-28a(+) by a single nucleotide. A mutagenesis primer used herein was a DNA consisting of the nucleotide sequence: 5'-ggctacattctggagacttagcttactgggacg-3' (SEQ ID NO: 8). The 5' ends of both primers had been phosphorylated in advance with T4 polynucleotide kinase (produced by TOYOBO). A recombinant plasmid was synthesized using T4 DNA polymerase and T4 DNA ligase provided with a Transformer site-directed mutagenesis kit. After cleavage treatment with Fsp I, recombinant plasmids that had not been cleaved with Fsp I were introduced into *Escherichia coli* mismatch repair deficient strain BMH71-18mutS, followed by culturing of *Escherichia coli*. The thus obtained recombinant plasmids were further cleaved with Fsp I, and then recombinant plasmids that had not been cleaved with Fsp I were selected as recombinant plasmids into which mutation had been introduced.

The nucleotide sequence of the mutant firefly luciferase gene (DNA) in the recombinant plasmid into which mutation had been introduced was determined using a DTCS Quick Start Master Mix kit and an electrophoresis analysis apparatus CEQ8000 (both produced by Beckman Coulter). The nucleotide sequence is as shown in SEQ ID NO: 9. It was thus confirmed that the mutant firefly luciferase gene in the recombinant plasmid encoded the mutant firefly luciferase consisting of the amino acid sequence derived from the amino acid sequence of North American firefly luciferase by substitution of isoleucine (Ile) at position 423 with leucine (Leu).

Preparation of Transformed *Escherichia coli*:

The recombinant plasmid containing the mutant firefly luciferase gene was introduced by a calcium chloride method into *Escherichia coli* (HMS174 (DE3) (produced by Novagen)) having genomic DNA into which a T7 RNA polymerase gene had been incorporated. The *Escherichia coli* was subjected to plate culture on selection agar medium containing 30 μg/mL kanamycin, so that transformed *Escherichia coli* was selected.

Collection and Purification of Mutant Firefly Luciferase:

Transformed *Escherichia coli* was subjected to shake culture for 2.5 hours using a shake culture system (produced by Takasaki Scientific Instrument Co., Ltd.) at 37° C. in 200 mL of 2×YT medium (containing 30 μg/mL kanamycin). 200 μL of 100 mM IPTG was then added so that the IPTG concentration in the medium reached 0.1 mM, followed by 6 hours of expression induction at 25° C. In addition, IPTG is an expression inducer that cancels the expression suppressed due to a lac repressor and induces T7 RNA polymerase.

Microbial bodies of *Escherichia coli* were collected by subjecting the culture solution to 5 minutes of centrifugation at 8000 rpm. The resultant was frozen at −20° C. and then preserved. The frozen microbial bodies were thawed with 5 mL of a binding buffer (20, mM $NaH_2PO_4$ (pH7.4) containing 500 mM NaCl and 20 mM imidazole), suspended, and then disrupted by ultrasound. The solution containing disrupted microbial bodies was centrifuged at 9000 rpm for 30 minutes. Thus, a mutant firefly luciferase (crude enzyme) solution as a supernatant was obtained.

A histidine tag had been added to the C-terminal side of the thus expressed mutant firefly luciferase. Hence, a crude enzyme was purified by nickel chelate affinity chromatography. First, a column (produced by PIERCE, Disposable Polystyrene Column) was filled with 0.5 mL of Ni Sepharose 6 Fast Flow (produced by Amersham Biosciences), followed by equilibration using a binding buffer. Next, 5 mL of a crude enzyme solution was added to the column and then the resultant was washed with a binding buffer. The mutant firefly luciferase was eluted with 2.5 mL of an elution buffer (20 mM $NaH_2PO_4$ (pH7.4) containing 500 mM NaCl and 500 mM imidazole). Furthermore, with the use of a PD-10 Desalting column (produced by Amersham Biosciences), the elution buffer was substituted with 3.5 mL of a reaction buffer (50 mM Tris-HCl buffer (pH7.4) containing 10 mM $MgCl_2$). The purified mutant firefly luciferase was thus obtained.

Measurement of the Luminescence Intensity of the Mutant Firefly Luciferase:

Protein quantification for the thus obtained mutant firefly luciferase was performed using Bio-Rad Protein Assay (produced by BIORAD) based on the Bradford method and IgG as a standard. A reaction buffer (50 μL) containing the mutant firefly luciferase (20 μg/mL) was added to a 96-well plate (produced by Nunc, LumiNunc plate). Subsequently, 50 μL of a substrate buffer (50 mM Tris-HCl buffer (pH 7.4) containing $2\times10^{-6}$ M D-firefly luciferin (produced by Wako Pure Chemical Industries, Ltd.), $2\times10^{-7}$ M ATP, and 10 mM $MgCl_2$) was added using an injector provided with a microplate reader (produced by Perkin-Elmer, ARVO MX). Subsequently, luminescence intensity was measured using the above microplate reader. Also for North American firefly luciferase (wild type), transformed *Escherichia coli* was prepared in a manner similar to that employed for the mutant firefly luciferase, except that a recombinant plasmid (pET-28a(+)) containing the North American firefly luciferase gene (cDNA) was used instead of the recombinant plasmid containing the mutant firefly luciferase gene. The enzyme was collected and purified and then the luminescence intensity of the enzyme was measured. Subsequently, the ratio (luminescence intensity ratio) of the luminescence intensity of the mutant firefly luciferase to that of North American firefly luciferase was found.

Examples 2 and 3 and Comparative Examples 1 to 8

Mutant firefly luciferases each consisting of an amino acid sequence derived from the amino acid sequence of North American firefly luciferase were produced as described below by substitution of isoleucine (Ile) at position 423 with methionine (Met) (Example 2), phenylalanine (Phe) (Example 3), valine (Val) (Comparative example 1), alanine (Ala) (Comparative example 2), glycine (Gly) (Comparative example 3), serine (Ser) (Comparative example 4), glutamine (Gln) (Comparative example 5), arginine (Arg) (Comparative example 6), lysine (Lys) (Comparative example 7), or glutamic acid (Glu) (Comparative example 8). Their firefly luciferase activity (luminescence intensity) was then measured.

The purified mutant firefly luciferases were obtained and then the luminescence intensity thereof was measured in a manner similar to that of Example 1, except that a DNA consisting of the nucleotide sequence below was used as a mutagenesis primer in site-specific mutagenesis. Subsequently, the ratio (luminescence intensity ratio) of the luminescence intensity of each mutant firefly luciferase to that of North American firefly luciferase was found using the luminescence intensity of North American firefly luciferase measured in Example 1. Furthermore, in a manner similar to that of Example 1, the nucleotide sequence of each mutant firefly luciferase gene (DNA) in the recombinant plasmids was determined. Thus, it was confirmed that the relevant gene encoded the target mutant firefly luciferase.

```
Example 2:
                                  (SEQ ID NO: 10)
5'-ggctacattctggagacatggcttactgggacg-3'

Example 3:
                                  (SEQ ID NO: 11)
5'-ggctacattctggagactttgcttactgggacg-3'

Comparative example 1:
                                  (SEQ ID NO: 12)
5'-ggctacattctggagacgtagcttactgggacg-3'

Comparative example 2:
                                  (SEQ ID NO: 13)
5'-ggctacattctggagacgcagcttactgggacg-3'

Comparative example 3:
                                  (SEQ ID NO: 14)
5'-ggctacattctggagacggagcttactgggacg-3'

Comparative example 4:
                                  (SEQ ID NO: 15)
5'-ggctacattctggagactcagcttactgggacg-3'

Comparative example 5:
                                  (SEQ ID NO: 16)
5'-ggctacattctggagaccaagcttactgggacg-3'
```

-continued
Comparative example 6:
                                        (SEQ ID NO: 17)
5'-ggctacattctggagacagagcttactgggacg-3'

Comparative example 7:
                                        (SEQ ID NO: 18)
5'-ggctacattctggagacaaagcttactgggacg-3'

Comparative example 8:
                                        (SEQ ID NO: 19)
5'-ggctacattctggagacgaagcttactgggacg-3'

Table 1 shows the results of Examples 1 to 3 and Comparative examples 1 to 8. In addition, the molecular weight, polarity, and electric charge of each of the above amino acids are as shown in Table 1. In Table 1, "polar" and "nonpolar" indicate that an amino acid has a polar group in its side chain and that an amino acid has a nonpolar group in its side chain, respectively. "Positively charged" and "negatively charged" indicate that an amino acid is positively charged and that an amino acid is negatively charged, respectively, at a physiological pH (pH 7.4). (The same applies to Table 2 and Table 3 shown later.)

TABLE 1

|  |  | Amino acid at position 423 | Molecular weight | Polarity/ electric charge | Luminescence intensity ratio |
|---|---|---|---|---|---|
| Wild type | North American firefly | Ile | 131 | Nonpolar | — |
| Mutant | Example 1 | Leu | 131 | Nonpolar | 4.3 |
|  | Example 2 | Met | 149 | Nonpolar | 3.5 |
|  | Example 3 | Phe | 165 | Nonpolar | 1.2 |
|  | Comparative example 1 | Val | 117 | Nonpolar | 1 |
|  | Comparative example 2 | Ala | 89 | Nonpolar | 0.3 |
|  | Comparative example 3 | Gly | 75 | Polar | <0.01 |
|  | Comparative example 4 | Ser | 105 | Polar | 0.03 |
|  | Comparative example 5 | Gln | 146 | Polar | 0.5 |
|  | Comparative example 6 | Arg | 174 | Positively charged | <0.01 |
|  | Comparative example 7 | Lys | 146 | Positively charged | <0.01 |
|  | Comparative example 8 | Glu | 147 | Negatively charged | 0.04 |

As is clear from Table 1, substitution of isoleucine (Ile) at position 423 with leucine (Leu), methionine (Met), or phenylalanine (Phe) resulted in luminescence intensity increased to a level 4.3 times, times, or 1.2 times greater than that of North American firefly luciferase. It was revealed by these results that luminescence intensity is sufficiently increased compared with that of North American firefly luciferase via substitution of an amino acid at position 423 with a nonpolar amino acid having a molecular weight that is the same as or higher than that of the amino acid in the amino acid sequence of North American firefly luciferase.

Examples 4 to 6 and Comparative Examples 9 to 11

Mutant firefly luciferases each consisting of an amino acid sequence derived from the amino acid sequence of North American firefly luciferase were produced as described below by substitution of aspartic acid (Asp) at position 436 with glycine (Gly) (Example 4), alanine (Ala) (Example 5), serine (Ser) (Example 6), asparagine (Asn) (Comparative example 9), glutamic acid (Glu) (Comparative example 10), or valine (Val) (Comparative example 11). Their firefly luciferase activity (luminescence intensity) was then measured.

The purified mutant firefly luciferases were obtained and then the luminescence intensity thereof was measured in a manner similar to that of Example 1, except that a DNA consisting of the following nucleotide sequence was used as a mutagenesis primer in site-specific mutagenesis. Subsequently, the ratio (luminescence intensity ratio) of the luminescence intensity of each mutant firefly luciferase to that of North American firefly luciferase was found using the luminescence intensity of North American firefly luciferase measured in Example 1. Furthermore, in a manner similar to that of Example 1, the nucleotide sequence of each mutant firefly luciferase gene (DNA) in recombinant plasmids was determined, so as to confirm that the relevant gene encoded the target mutant firefly luciferase.

Example 4:
                                        (SEQ ID NO: 20)
5'-cacttcttcatagttggccgcttgaagtc-3'

Example 5:
                                        (SEQ ID NO: 21)
5'-cacttcttcatagttgcccgcttgaagtc-3'

Example 6:
                                        (SEQ ID NO: 22)
5'-cacttcttcatagttagccgcttgaagtc-3'

Comparative example 9:
                                        (SEQ ID NO: 23)
5'-cacttcttcatagttaaccgcttgaagtc-3'

Comparative example 10:
                                        (SEQ ID NO: 24)
5'-cacttcttcatagttgaacgcttgaagtc-3'

Comparative example 11:
                                        (SEQ ID NO: 25)
5'-cacttcttcatagttgtccgcttgaagtc-3'

Table 2 shows the results of Examples 4 to 6 and Comparative examples 9 to 11. Furthermore, the molecular weight, and polarity or electric charge of each of the above amino acids are as shown in Table 2.

TABLE 2

|  |  | Amino acid at position 436 | Molecular weight | Polarity/ electric charge | Luminescence intensity ratio |
|---|---|---|---|---|---|
| Wild type | North American firefly | Asp | 133 | Negatively charged | — |
| Mutant | Example 4 | Gly | 75 | Polar | 12.1 |
|  | Example 5 | Ala | 89 | Nonpolar | 6.3 |
|  | Example 6 | Ser | 105 | Polar | 2.3 |
|  | Comparative example 9 | Asn | 132 | Polar | 0.5 |
|  | Comparative example 10 | Glu | 147 | Negatively charged | 0.47 |
|  | Comparative example 11 | Val | 117 | Nonpolar | <0.01 |

As is clear from Table 2, substitution of aspartic acid (Asp) at position 436 with glycine (Gly), alanine (Ala), or serine (Ser) resulted in luminescence intensity increased to a level 12.1 times, 6.3 times, or 2.3 times greater than that of North American firefly luciferase. It was revealed by these results that luminescence intensity is sufficiently increased compared with that of North American firefly luciferase via substitution of an amino acid at position 436 in the amino acid sequence of North American firefly luciferase with an amino acid that has a molecular weight lower than that of the amino acid and is selected from among glycine, alanine, and serine.

Examples 7 to 9 and Comparative Examples 12 to 19

Mutant firefly luciferases each consisting of an amino acid sequence derived from the amino acid sequence of North American firefly luciferase were produced as described below by substitution of leucine (Leu) at position 530 with arginine (Arg) (Example 7), lysine (Lys) (Example 8), histidine (His) (Example 9), valine (Val) (Comparative example 12), isoleucine (Ile) (Comparative example 13), alanine (Ala) (Comparative example 14), proline (Pro) (Comparative example 15), phenylalanine (Phe) (Comparative example 16), aspartic acid (Asp) (Comparative example 17), serine (Ser) (Comparative example 18), or tyrosine (Tyr) (Comparative example 19). Their firefly luciferase activity (luminescence intensity) was measured.

The purified mutant firefly luciferases were obtained and then the luminescence intensity thereof was measured in a manner similar to that of Example 1, except that a DNA consisting of the nucleotide sequence was used as a mutagenesis primer in site-specific mutagenesis. Subsequently, the ratio (luminescence intensity ratio) of the luminescence intensity of each mutant firefly luciferase to that of North American firefly luciferase was found using the luminescence intensity of North American firefly luciferase measured in Example 1. Furthermore, in a manner similar to that of Example 1, the nucleotide sequence of each mutant firefly luciferase gene (DNA) in recombinant plasmids was determined, so as to confirm that the relevant gene encoded the target mutant firefly luciferase.

```
Example 7:
                              (SEQ ID NO: 26)
5'-ccggaaaacgcgacgcaag-3'

Example 8:
                              (SEQ ID NO: 27)
5'-ggtcttaccggaaaaaaggacgcaag-3'

Example 9:
                              (SEQ ID NO: 28)
5'-ccggaaaacacgacgcaag-3'

Comparative example 12:
                              (SEQ ID NO: 29)
5'-ggtcttaccggaaaagtcgacgcaag-3'

Comparative example 13:
                              (SEQ ID NO: 30)
5'-ggtcttaccggaaaaatcgacgcaag-3'

Comparative example 14:
                              (SEQ ID NO: 31)
5'-ggtcttaccggaaaagccgacgcaag-3'

Comparative example 15:
                              (SEQ ID NO: 32)
5'-ggtcttaccggaaaacccgacgcaag-3'

Comparative example 16:
                              (SEQ ID NO: 33)
5'-ggtcttaccggaaaattcgacgcaag-3'

Comparative example 17:
                              (SEQ ID NO: 34)
5'-ggtcttaccggaaaagacgacgcaag-3'

Comparative example 18:
                              (SEQ ID NO: 35)
5'-ggtcttaccggaaaaagcgacgcaag-3'

Comparative example 19:
                              (SEQ ID NO: 36)
5'-ggtcttaccggaaaatacgacgcaag-3'
```

Table 3 shows the results of Examples 7 to 9 and Comparative examples 12 to 19. Furthermore, the isoelectric point and polarity or electric charge of each of the above amino acids are as shown in Table 3.

TABLE 3

| | | Amino acid at position 530 | Isoelectric point | Polarity/ electric charge | Luminescence intensity ratio |
|---|---|---|---|---|---|
| Wild type | North American firefly | Leu | 6.0 | Nonpolar | — |
| Mutant | Example 7 | Arg | 10.8 | Positively charged | 11.8 |
| | Example 8 | Lys | 9.7 | Positively charged | 3.3 |
| | Example 9 | His | 7.6 | Positively charged | 2.3 |
| | Comparative example 12 | Val | 6.0 | Nonpolar | 0.77 |
| | Comparative example 13 | Ile | 6.0 | Nonpolar | 0.68 |
| | Comparative example 14 | Ala | 6.0 | Nonpolar | 0.17 |
| | Comparative example 15 | Pro | 6.3 | Nonpolar | 0.04 |
| | Comparative example 16 | Phe | 5.5 | Nonpolar | 0.03 |
| | Comparative example 17 | Asp | 2.8 | Negatively charged | 0.3 |
| | Comparative example 18 | Ser | 5.7 | Polar | 0.15 |
| | Comparative example 19 | Tyr | 5.7 | Polar | 0.17 |

As is clear from Table 3, substitution of leucine (Leu) at position 530 with arginine (Arg), lysine (Lys), or histidine (His) resulted in luminescence intensity increased to a level 11.8 times, 3.3 times, or 2.3 times greater than that of North American firefly luciferase. It was revealed by these results that luminescence intensity is sufficiently increased compared with that of North American firefly luciferase via substitution of an amino acid at position 530 in the amino acid sequence of North American firefly luciferase with a positively-charged amino acid having an isoelectric point higher than that of the amino acid.

Example 10

A mutant firefly luciferase consisting of an amino acid sequence derived from the amino acid sequence of North American firefly luciferase was produced as described below by substitution of isoleucine (Ile) at position 423 with leucine (Leu) and substitution of aspartic acid (Asp) at position 436 with glycine (Gly). Its firefly luciferase activity (luminescence intensity) was measured.

The recombinant plasmid into which the mutation had been introduced in Example 4 (that is, a recombinant plasmid containing a gene encoding a mutant firefly luciferase in which aspartic acid (Asp) at position 436 had been substituted with glycine (Gly)), was cleaved with restriction enzymes Nco I and Xho I (both produced by New England Biolabs). After separation by agarose gel electrophoresis, only DNA fragments containing the mutant firefly luciferase gene in which aspartic acid (Asp) at position 436 had been substituted with glycine (Gly) were collected. Subsequently, the DNA fragment was incorporated into a plasmid (pET-28a(+) plasmid DNA (produced by Novagen)) that had been cleaved with Nco I and Xho I in advance using a DNA Ligation Kit (produced by BioDynamics Laboratory). The purified mutant firefly luciferase was obtained and then the luminescence intensity thereof was measured in a manner similar to that used in Example 1, except that the thus obtained recombinant plasmid was used as a template in site-specific mutagenesis. Subsequently, the ratio (luminescence intensity ratio) of the luminescence intensity of the mutant firefly luciferase to that of North American firefly luciferase was found using the luminescence intensity of North American firefly luciferase measured in Example 1.

Furthermore, the nucleotide sequence of the mutant firefly luciferase gene in such a recombinant plasmid into which the mutation had been introduced was determined in a manner similar to that used in Example 1. The nucleotide sequence is as shown in SEQ ID NO: 37. It was thus confirmed that the mutant firefly luciferase gene in the recombinant plasmids encoded the mutant firefly luciferase consisting of the amino acid sequence derived from the amino acid sequence of North American firefly luciferase by substitution of isoleucine (Ile) at position 423 with leucine (Leu) and substitution of aspartic acid (Asp) at position 436 with glycine (Gly).

The luminescence intensity of the mutant firefly luciferase in which substitution of isoleucine (Ile) at position 423 with leucine (Leu) and substitution of aspartic acid (Asp) at position 436 with glycine (Gly) had taken place in combination was increased to a level 18 times greater than that of North American firefly luciferase and 1.5 times greater than that of the mutant firefly luciferase (Example 4) in which substitution of aspartic acid at position 436 with glycine had taken place independently. It was revealed by these results that luminescence intensity is significantly increased compared with that of North American firefly luciferase via substitution of an amino acid at position 423 with a nonpolar amino acid having a molecular weight that is the same as or higher than that of the amino acid and substitution of an amino acid at position 436 with an amino acid that has a molecular weight lower than that of the amino acid and is selected from among glycine, alanine, and serine.

Example 11

A mutant firefly luciferase consisting of an amino acid sequence derived from the amino acid sequence of North American firefly luciferase was produced as described below by substitution of isoleucine (Ile) at position 423 with leucine (Leu) and substitution of leucine (Leu) at position 530 with arginine (Arg). Its firefly luciferase activity (luminescence intensity) was then measured.

The recombinant plasmid into which the mutation had been introduced in Example 7 (that is, a recombinant plasmid containing a gene encoding a mutant firefly luciferase in which leucine (Leu) at position 530 had been substituted with arginine (Arg)) was cleaved with restriction enzymes Nco I and Xho I (both produced by New England Biolabs). After separation by agarose gel electrophoresis, only DNA fragments containing the mutant firefly luciferase gene in which leucine (Leu) at position 530 had been substituted with arginine (Arg) were collected. Subsequently, the DNA fragment was incorporated into a plasmid (pET-28a(+) plasmid DNA (produced by Novagen)) that had been cleaved with Nco I and Xho I in advance using a DNA Ligation Kit (produced by BioDynamics Laboratory). The purified mutant firefly luciferase was obtained and then the luminescence intensity thereof was measured in a manner similar to that of Example 1, except that the thus obtained recombinant plasmid was used as a template in site-specific mutagenesis. Subsequently, the ratio (luminescence intensity ratio) of the luminescence intensity of the mutant firefly luciferase to that of North American firefly luciferase was found using the luminescence intensity of North American firefly luciferase measured in Example 1.

Furthermore, the nucleotide sequence of the mutant firefly luciferase gene in such a recombinant plasmid in which the mutation had been introduced was determined in a manner similar to that of Example 1. The nucleotide sequence is as shown in SEQ ID NO: 38. It was thus confirmed that the mutant firefly luciferase gene in the recombinant plasmids encoded a mutant firefly luciferase consisting of the amino acid sequence derived from the amino acid sequence of North American firefly luciferase by substitution of isoleucine (Ile) at position 423 with leucine (Leu) and substitution of leucine (Leu) at position 530 with arginine (Arg).

The luminescence intensity of the mutant firefly luciferase in which substitution of isoleucine (Ile) at position 423 with leucine (Leu) and that of leucine (Leu) at position 530 with arginine (Arg) had taken place in combination was increased to a level 18 times greater than that of North American firefly luciferase and 1.5 times greater than that of the mutant firefly luciferase (Example 7) in which substitution of leucine at position 530 with arginine had taken place independently. It was revealed by these results that luminescence intensity is significantly increased compared with that of North American firefly luciferase via substitution of an amino acid at position 423 with a nonpolar amino acid having a molecular weight that is the same as or higher than that of the amino acid and substitution of an amino acid at position 530 with a positively-charged amino acid having an isoelectric point higher than that of the amino acid.

Example 12

A mutant firefly luciferase consisting of an amino acid sequence derived from the amino acid sequence of North American firefly luciferase was produced as described below by substitution of aspartic acid (Asp) at position 436 with glycine (Gly) and substitution of leucine (Leu) at position 530 with arginine (Arg). Its firefly luciferase activity (luminescence intensity) was then measured.

The recombinant plasmid into which the mutation had been introduced in Example 7 (that is, a recombinant plasmid containing a gene encoding a mutant firefly luciferase in which leucine (Leu) at position 530 had been substituted with arginine (Arg)) was cleaved with restriction enzymes Nco I and Xho I (both produced by New England Biolabs). After separation by agarose gel electrophoresis, only DNA fragments containing the mutant firefly luciferase gene in which leucine (Leu) at position 530 had been substituted with arginine (Arg) were collected. Subsequently, the DNA fragment was incorporated into a plasmid (pET-28a(+) plasmid DNA (produced by Novagen)) that had been cleaved with Nco I and Xho I in advance using a DNA Ligation Kit (produced by BioDynamics Laboratory). The purified mutant firefly luciferase was obtained and then the luminescence intensity thereof was measured in a manner similar to that of Example 4, except that the thus obtained recombinant plasmid was used as a template in site-specific mutagenesis. Subsequently, the ratio (luminescence intensity ratio) of the luminescence intensity of the mutant firefly luciferase to that of North American firefly luciferase was found using the luminescence intensity of North American firefly luciferase measured in Example 1.

Furthermore, the nucleotide sequence of the mutant firefly luciferase gene in such a recombinant plasmid in which the mutation had been introduced was determined in a manner similar to that of Example 1. The nucleotide sequence is as shown in SEQ ID NO: 39. It was thus confirmed that the mutant firefly luciferase gene in the recombinant plasmids encoded a mutant firefly luciferase consisting of the amino acid sequence derived from the amino acid sequence of North American firefly luciferase by substitution of aspartic acid (Asp) at position 436 with glycine (Gly) and substitution of leucine (Leu) at position 530 with arginine (Arg).

The luminescence intensity of the mutant firefly luciferase in which substitution of aspartic acid (Asp) at position 436 with glycine (Gly) and substitution of leucine (Leu) at position 530 with arginine (Arg) had taken place in combination was increased to a level 8 times greater than that of North American firefly luciferase. It was revealed by these results that luminescence intensity is sufficiently increased compared with that of North American firefly luciferase via substitution of an amino acid at position 436 with an amino acid having a molecular weight lower than that of the amino acid and is selected from among glycine, alanine, and serine and substitution of an amino acid at position 530 with a positively-charged amino acid having an isoelectric point higher than that of the amino acid.

Example 13

A mutant firefly luciferase consisting of an amino acid sequence derived from the amino acid sequence of North American firefly luciferase was produced as described below by substitution of isoleucine (Ile) at position 423 with leucine (Leu), substitution of aspartic acid (Asp) at position 436 with glycine (Gly), and substitution of leucine (Leu) at position 530 with arginine (Arg). Its firefly luciferase activity (luminescence intensity) was then measured.

The recombinant plasmid into which the mutation had been introduced in Example 12 (that is, a recombinant plasmid containing a gene encoding a mutant firefly luciferase in which aspartic acid (Asp) at position 436 had been substituted with glycine (Gly) and (Leu) at position 530 had been substituted with arginine (Arg)) was cleaved with restriction enzymes Nco I and Xho I (both produced by New England Biolabs). After separation by agarose gel electrophoresis, only DNA fragments containing the mutant firefly luciferase gene in which aspartic acid (Asp) at position 436 had been substituted with glycine (Gly) and leucine (Leu) at position 530 had been substituted with arginine (Arg) were collected. Subsequently, the DNA fragment was incorporated into a plasmid (pET-28a(+) plasmid DNA (produced by Novagen)) that had been cleaved with Nco I and Xho I in advance using a DNA Ligation Kit (produced by BioDynamics Laboratory). The purified mutant firefly luciferase was obtained and then the luminescence intensity thereof was measured in a manner similar to that of Example 1, except that the thus obtained recombinant plasmid was used as a template in site-specific mutagenesis. Subsequently, the ratio (luminescence intensity ratio) of the luminescence intensity of the mutant firefly luciferase to that of North American firefly luciferase was found using the luminescence intensity of North American firefly luciferase measured in Example 1.

Furthermore, the nucleotide sequence of the mutant firefly luciferase gene in such a recombinant plasmid in which the mutation had been introduced was determined in a manner similar to that of Example 1. The nucleotide sequence is as shown in SEQ ID NO: 40. It was thus confirmed that the mutant firefly luciferase gene in the recombinant plasmid encoded a mutant firefly luciferase consisting of the amino acid sequence derived from the amino acid sequence of North American firefly luciferase by substitution of isoleucine (Ile) at position 423 with leucine (Leu), substitution of aspartic acid (Asp) at position 436 with glycine (Gly), and substitution of leucine (Leu) at position 530 with arginine (Arg).

The luminescence intensity of the mutant firefly luciferase in which substitution of isoleucine (Ile) at position 423 with leucine (Leu), substitution of aspartic acid (Asp) at position 436 with glycine (Gly), and substitution of leucine (Leu) at position 530 with arginine (Arg) had taken place in combination was increased to a level 20 times greater than that of North American firefly luciferase. It was revealed by these results that luminescence intensity is significantly increased compared with that of North American firefly luciferase via substitution of an amino acid at position 423 with nonpolar amino acid having a molecular weight that is the same as or higher than that of the amino acid, substitution of an amino acid at position 436 with an amino acid that has a molecular weight lower than that of the amino acid and is selected from among glycine, alanine, and serine, and substitution of an amino acid at position 530 with a positively-charged amino acid having an isoelectric point higher than that of the amino acid.

Example 14

A mutant firefly luciferase consisting of an amino acid sequence derived from the amino acid sequence of North American firefly luciferase was produced as described below by substitution of isoleucine (Ile) at position 423 with leucine (Leu), substitution of leucine (Leu) at position 530 with arginine (Arg), substitution of isoleucine (Ile) at position 47 with threonine (Thr), substitution of asparagine (Asn) at position 50 with serine (Ser), substitution of methionine (Met) at position 59 with threonine (Thr), and substitution of threonine (Thr) at position 252 with serine (Ser). Its firefly luciferase activity (luminescence intensity) was then measured.

The recombinant plasmid into which the mutation had been introduced in Example 11 (that is, a recombinant plasmid containing a gene encoding a mutant firefly luciferase in which isoleucine (Ile) at position 423 had been substituted with leucine (Leu) and leucine (Leu) at position 530 had been substituted with arginine (Arg)) was cleaved with restriction enzymes Nco I and Xho I (both produced by New England Biolabs). After separation by agarose gel electrophoresis, only DNA fragments containing the mutant firefly luciferase gene in which isoleucine (Ile) at position 423 had been substituted with leucine (Leu) and leucine (Leu) at position 530 had been substituted with arginine (Arg) were collected. Subsequently, the DNA fragment was incorporated into a plasmid (pET-28a(+) plasmid DNA (produced by Novagen)) that had been cleaved with Nco I and Xho I in advance using a DNA Ligation Kit (produced by BioDynamics Laboratory). Site-specific mutagenesis was performed in a manner similar to that of Example 1 except that the thus obtained recombinant plasmid was used as a template and a DNA consisting of the nucleotide sequence: 5'-gatgcacataccgaggtgaac-3' (SEQ ID NO: 41) was used as a mutagenesis primer.

Next, the thus obtained recombinant plasmid was cleaved with restriction enzymes Nco I and Xho I (both produced by New England Biolabs). After separation by agarose gel electrophoresis, only DNA fragments containing the mutant firefly luciferase gene in which isoleucine (Ile) at position 423 had been substituted with leucine (Leu), leucine (Leu) at position 530 had been substituted with arginine (Arg), and isoleucine (Ile) at position 47 had been substituted with threonine (Thr) were collected. Subsequently, the DNA fragment was incorporated into a plasmid (pET-28a(+)) that had been cleaved with Nco I and Xho I in advance using a DNA Ligation Kit (produced by BioDynamics Laboratory). Site-specific mutagenesis was performed in a manner similar to that of Example 1 except that the thus obtained recombinant plasmid was used as a template and a DNA consisting of the nucleotide sequence: 5'-catatcgaggtgagcatcacgtacgcg-3' (SEQ ID NO: 42) was used as a mutagenesis primer.

Next, the thus obtained recombinant plasmid was cleaved with restriction enzymes Nco I and Xho I (both produced by New England Biolabs). After separation by agarose gel electrophoresis, only DNA fragments containing the mutant firefly luciferase gene in which isoleucine (Ile) at position 423 had been substituted with leucine (Leu), leucine (Leu) at position 530 had been substituted with arginine (Arg), isoleucine (Ile) at position 47 had been substituted with threonine (Thr), and asparagine (Asn) at position 50 had been substituted with serine (Ser) were collected. Subsequently, the DNA fragment was incorporated into a plasmid (pET-28a(+)) that had been cleaved with Nco I and Xho I in advance using a DNA Ligation Kit (produced by BioDynamics Laboratory). Site-specific mutagenesis was performed in a manner similar to that of Example 1 except that the thus obtained recombinant plasmid was used as a template and a DNA consisting of the nucleotide sequence: 5'-gcggaatacttcgaaacgtccgttcgg-3' (SEQ ID NO: 43) was used as a mutagenesis primer.

Finally, the thus obtained recombinant plasmid was cleaved with restriction enzymes Nco I and Xho I (both produced by New England Biolabs). After separation by agarose gel electrophoresis, only DNA fragments containing the mutant firefly luciferase gene in which isoleucine (Ile) at position 423 had been substituted with leucine (Leu), leucine (Leu) at position 530 had been substituted with arginine (Arg), isoleucine (Ile) at position 47 had been substituted with threonine (Thr), asparagine (Asn) at position 50 had been substituted with serine (Ser), and methionine (Met) at position 59 had been substituted with threonine (Thr) were collected. Subsequently, the DNA fragment was incorporated into a plasmid (pET-28a(+)) that had been cleaved with Nco I and Xho I in advance using a DNA Ligation Kit (produced by BioDynamics Laboratory). The purified mutant firefly luciferase was obtained and then the luminescence intensity thereof was measured in a manner similar to that of Example 1, except that the thus obtained recombinant plasmid was used as a template and a DNA consisting of the nucleotide sequence: 5'-ggaatgtttacttcactcgg-3' (SEQ ID NO: 44) was used as a mutagenesis primer. Subsequently, the ratio (luminescence intensity ratio) of the luminescence intensity of the mutant firefly luciferase to that of North American firefly luciferase was found using the luminescence intensity of North American firefly luciferase measured in Example 1.

Furthermore, the nucleotide sequence of the mutant firefly luciferase gene in such a recombinant plasmid in which the mutation had been introduced was determined in a manner similar to that of Example 1. The nucleotide sequence is as shown in SEQ ID NO: 45. It was thus confirmed that the mutant firefly luciferase gene in the recombinant plasmid encoded a mutant firefly luciferase consisting of the amino acid sequence derived from the amino acid sequence of North American firefly luciferase by substitution of isoleucine (Ile) at position 423 with leucine (Leu), that of leucine (Leu) at position 530 with arginine (Arg), that of isoleucine (Ile) at position 47 with threonine (Thr), that of asparagine (Asn) at position 50 with serine (Ser), that of methionine (Met) at position 59 with threonine (Thr), and that of threonine (Thr) at position 252 with serine (Ser).

The luminescence intensity of the mutant firefly luciferase was increased to a level 21 times greater than that of North American firefly luciferase or to a level 1.2 times greater than that of the mutant firefly luciferase (Example 11) in which substitution of isoleucine (Ile) at position 423 with leucine (Leu) and substitution of leucine (Leu) at position 530 with arginine (Arg) alone had taken place. It was revealed by these results that luminescence intensity is significantly increased compared with that of North American firefly luciferase via substitution of an amino acid at position 423 with a nonpolar amino acid having a molecular weight that is the same as or higher than that of the amino acid, substitution of an amino acid at position 530 with a positively-charged amino acid having an isoelectric point higher than that of the amino acid, substitution of isoleucine at position 47 with threonine, substitution of asparagine at position 50 with serine, substitution of methionine at position 59 with threonine, and substitution of threonine at position 252 with serine in the amino acid sequence of North American firefly luciferase.

Example 15

A mutant firefly luciferase consisting of an amino acid sequence derived from the amino acid sequence of Heike firefly luciferase was produced as described below by substitution of isoleucine (Ile) at position 425 with leucine (Leu). Its firefly luciferase activity (luminescence intensity) was then measured.

Heike firefly (*Luciola lateralis*) larvae were frozen with liquid nitrogen and then disrupted using a mortar. Total RNA of Heike firefly was extracted using Total RNA extraction kit (NucleoSpin RNA L (produced by MACHEREY-NAGEL)). Subsequently, Heike firefly luciferase cDNA (the nucleotide sequence is as shown in SEQ ID NO: 48) was prepared using a DNA consisting of the nucleotide sequence: 5'-gactcatatg-gaaaacatggagaacgatg-3' (SEQ ID NO: 46) containing a restriction enzyme Nde I recognition sequence and a DNA consisting of the nucleotide sequence: 5'-gacactcgagcatcttag-caactgg-3' (SEQ ID NO: 47) containing an Xho I recognition sequence as primers and an RT-PCR kit (SuperScriptIII One-Step RT-PCR System with Platinum Taq DNA Polymerase (produced by Invitrogen)). The thus obtained cDNA was cleaved with Nde I and Xho I (both produced by New England Biolabs). The resultant was then incorporated into a plasmid (pET-30a(+) plasmid DNA (produced by Novagen)) that had been cleaved with Nde I and Xho I in advance using a DNA Ligation Kit (produced by BioDynamics Laboratory). In addition, pET-30a(+) contained a T7 promoter and a T7 terminator. Furthermore, pET-30a(+) contained a gene encoding a histidine tag in the vicinity of the cloning site, so that the histidine tag was added to the C-terminal side of the target protein to be expressed. Moreover, pET-30a(+) had kanamycin resistance.

Next, site-specific mutagenesis was performed using the thus obtained recombinant plasmid as a template and a Transformer site-directed mutagenesis kit (produced by Clontech).

A selection primer used herein was a DNA consisting of the nucleotide sequence: 5'-gttaagccagtttacactccgc-3' (SEQ ID NO: 49) that contains a sequence differing from a restriction enzyme Bst1107 I recognition sequence in pET-30a(+) by a single nucleotide. A mutagenesis primer used herein was a DNA consisting of the nucleotide sequence: 5'-ggttggttgca-cacaggagatcttgggtattacg-3' (SEQ ID NO: 50). The 5' ends of both primers had been phosphorylated in advance with T4 polynucleotide kinase (produced by TOYOBO). A recombinant plasmid was synthesized using T4 DNA polymerase and T4 DNA ligase provided with a Transformer site-directed mutagenesis kit. After cleavage treatment with Bst1107 I, recombinant plasmids that had not been cleaved with Bst1107 I were introduced into *Escherichia coli* mismatch repair deficient strain BMH71-18mutS, followed by culturing of *Escherichia coli*. The thus obtained recombinant plasmids were further cleaved with Bst1107 I, and then recombinant plasmids that had not been cleaved with Bst1107 I were selected as recombinant plasmids into which mutation had been introduced. Transformed *Escherichia coli* was prepared in a manner similar to that of Example 1 except that the thus obtained recombinant plasmid was introduced into *Escherichia coli*. The mutant firefly luciferase was collected and purified. Furthermore, the nucleotide sequence of the mutant firefly luciferase gene (DNA) in the recombinant plasmids was determined in a manner similar to that of Example 1. It was thus confirmed that the gene encoded the target mutant firefly luciferase.

Protein quantification for the thus obtained mutant firefly luciferase was performed using Bio-Rad Protein Assay (produced by BIORAD) based on the Bradford method and IgG as a standard. After addition of 50 μL of a reaction buffer containing mutant firefly luciferase (0.1 mg/mL) to a 96-well plate (LumiNunc plate produced by Nunc), 50 μL of a 50 mM Tris-HCl buffer (pH7.4)) containing a substrate buffer ($1 \times 10^{-7}$ M D-firefly luciferin (produced by Wako Pure Chemical Industries, Ltd.), $1 \times 10^{-6}$ M ATP, and 10 mM $MgCl_2$) was added using an injector provided with a microplate reader (ARVO MX produced by Perkin-Elmer). Subsequently, luminescence intensity was measured using the above microplate reader.

Also for Heike firefly luciferase (wild type), transformed *Escherichia coli* was prepared in a manner similar to that employed for the mutant firefly luciferase except that a recombinant plasmid (pET-30a(+)) containing the above-obtained Heike firefly luciferase gene (cDNA) was used instead of a recombinant plasmid containing the mutant firefly luciferase gene. The enzyme was collected and then purified. The luminescence intensity of the enzyme was measured. Subsequently, the ratio (luminescence intensity ratio) of the luminescence intensity of the mutant firefly luciferase to that of Heike firefly luciferase was found.

Example 16

A mutant firefly luciferase consisting of an amino acid sequence derived from the amino acid sequence of Heike firefly luciferase was produced as described below by substitution of aspartic acid (Asp) at position 438 with glycine (Gly). Its firefly luciferase activity (luminescence intensity) was then measured.

The purified mutant firefly luciferase was obtained and then the luminescence intensity thereof was measured in a manner similar to that of Example 15, except that a DNA consisting of the nucleotide sequence: 5'-ctt-tatcgtgggtcgtttgaagtc-3' (SEQ ID NO: 51) was used as a mutagenesis primer in site-specific mutagenesis. Subsequently, the ratio (luminescence intensity ratio) of the luminescence intensity of the mutant firefly luciferase to that of Heike firefly luciferase was found using the luminescence intensity of Heike firefly luciferase measured in Example 15. Furthermore, in a manner similar to that of Example 1, the nucleotide sequence of the mutant firefly luciferase gene (DNA) in the recombinant plasmids was determined. Thus, it was confirmed that the relevant gene encoded the target mutant firefly luciferase.

Example 17

A mutant firefly luciferase consisting of an amino acid sequence derived from the amino acid sequence of Heike firefly luciferase was produced as described below by substitution of isoleucine (Ile) at position 532 with arginine (Arg). Its firefly luciferase activity (luminescence intensity) was then measured.

The purified mutant firefly luciferase was obtained and then the luminescence intensity thereof was measured in a manner similar to that of Example 15, except that a DNA consisting of the nucleotide sequence: 5'-ggtcttactggtaaaagg-gacggtaaagc-3' (SEQ ID NO: 52) was used as a mutagenesis primer in site-specific mutagenesis. Subsequently, the ratio (luminescence intensity ratio) of the luminescence intensity of the mutant firefly luciferase to that of Heike firefly luciferase was found using the luminescence intensity of Heike firefly luciferase measured in Example 15. Furthermore, in a manner similar to that of Example 1, the nucleotide sequence of the mutant firefly luciferase gene (DNA) in recombinant plasmids was determined. Thus, it was confirmed that the relevant gene encoded the target mutant firefly luciferase.

Example 18

A mutant firefly luciferase consisting of an amino acid sequence derived from the amino acid sequence of Heike firefly luciferase was produced by substitution of isoleucine (Ile) at position 425 with leucine (Leu) in a manner similar to that of Example 15. Its firefly luciferase activity (luminescence intensity) was measured. Also for North American firefly luciferase (wild type), a purified enzyme was obtained and then the luminescence intensity thereof was measured in a manner similar to that of Example 1. Subsequently, the ratio (luminescence intensity ratio) of the luminescence intensity of the mutant firefly luciferase to that of North American firefly luciferase was found. Furthermore, in a manner similar to that of Example 1, the nucleotide sequence of the mutant firefly luciferase gene (DNA) in the recombinant plasmids was determined. Thus, it was confirmed that the relevant gene encoded the target mutant firefly luciferase.

Example 19

A mutant firefly luciferase consisting of an amino acid sequence derived from the amino acid sequence of Heike firefly luciferase was produced by substitution of aspartic acid (Asp) at position 438 with glycine (Gly) in a manner similar to that of Example 16. Its firefly luciferase activity (luminescence intensity) was measured. Subsequently, the ratio (luminescence intensity ratio) of the luminescence intensity of the mutant firefly luciferase to that of North American firefly luciferase was found using the luminescence intensity of North American firefly luciferase measured in Example 18. Furthermore, in a manner similar to that of Example 1, the nucleotide sequence of the mutant firefly luciferase gene (DNA) in the recombinant plasmids was determined. Thus, it was confirmed that the relevant gene encoded the target mutant firefly luciferase.

Comparative Example 20

A mutant firefly luciferase consisting of an amino acid sequence derived from the amino acid sequence of Heike firefly luciferase was produced by substitution of isoleucine (Ile) at position 532 with arginine (Arg) in a manner similar to that of Example 17. Its firefly luciferase activity (luminescence intensity) was measured. Subsequently, the ratio (luminescence intensity ratio) of the luminescence intensity of the mutant firefly luciferase to that of North American firefly luciferase was found using the luminescence intensity of North American firefly luciferase measured in Example 18. Furthermore, in a manner similar to that of Example 1, the nucleotide sequence of the mutant firefly luciferase gene (DNA) in the recombinant plasmids was determined. Thus, it was confirmed that the relevant gene encoded the target mutant firefly luciferase.

Table 4 shows the results of Examples 15 to 19 and Comparative example 20. In addition, the amino acid sequence of Heike firefly luciferase and the amino acid sequence of North American firefly luciferase share 68% homology.

TABLE 4

| | | Luminescence intensity (cps) | Luminescence intensity ratio |
|---|---|---|---|
| Wild type | Heike firefly | 1596 | — |
| Mutant | Example 15 | 4097 | 2.6 |
| | Example 16 | 9539 | 6.0 |
| | Example 17 | 1966 | 1.2 |
| Wild type | North American firefly | 2972 | — |
| Mutant | Example 18 | 4097 | 1.4 |
| | Example 19 | 9539 | 3.2 |
| | Comparative example 20 | 1966 | 0.7 |

As is clear from Table 4, substitution of isoleucine (Ile) at position 425 with leucine (Leu), substitution of aspartic acid (Asp) at position 438 with glycine (Gly), and substitution of isoleucine (Ile) at position 532 with arginine (Arg) in the amino acid sequence of Heike firefly luciferase resulted in luminescence intensity increased to levels times, 6.0 times, and 1.2 times greater, respectively, than that of Heike firefly luciferase. It was revealed by these results that a mutant firefly luciferase consisting of a mutant amino acid sequence derived from the amino acid sequence of Heike firefly luciferase by the following substitution (a), (b), or (c) has luminescence intensity sufficiently higher than that of Heike firefly luciferase.

(a) Substitution of an amino acid at position 425 with a nonpolar amino acid having a molecular weight that is the same as or higher than that of the amino acid.

(b) Substitution of an amino acid at position 438 with an amino acid that has a molecular weight lower than that of the amino acid and is selected from among glycine, alanine, and serine.

(c) Substitution of an amino acid at position 532 with a positively-charged amino acid having an isoelectric point higher than that of the amino acid.

Furthermore, as is clear from Table 4, substitution of isoleucine (Ile) at position 425 with leucine (Leu) and substitution of aspartic acid (Asp) at position 438 with glycine (Gly) in the amino acid sequence of Heike firefly luciferase resulted in luminescence intensity increased to levels 1.4 times and 3.2 times greater, respectively, than that of North American firefly luciferase. It was revealed by these results the presence of mutant firefly luciferases each having luminescence intensity sufficiently higher than that of North American firefly luciferase among mutant firefly luciferases each consisting of a mutant amino acid sequence derived from the amino acid sequence of North American firefly luciferase by at least substitution (a) or (b) above and having 68% homology with the amino acid sequence of North American firefly luciferase.

Example 20

A mutant firefly luciferase consisting of an amino acid sequence derived from the amino acid sequence of Genji firefly luciferase was produced as described below by substitution of isoleucine (Ile) at position 425 with leucine (Leu). Its firefly luciferase activity (luminescence intensity) was then measured.

Genji firefly (*Luciola cruciata*) larvae were frozen with liquid nitrogen and then disrupted using a mortar. Total RNA of Genji firefly was extracted using Total RNA extraction kit (NucleoSpin RNA L (produced by MACHEREY-NAGEL)). Subsequently, Genji firefly luciferase cDNA (nucleotide sequence is as shown in SEQ ID NO: 54) was prepared using a DNA consisting of the nucleotide sequence: 5'-gactccatg-gaaaacatggaaaacgatg-3' (SEQ ID NO: 53) containing a restriction enzyme Nco I recognition sequence and a DNA consisting of the nucleotide sequence: 5'-gacactcgagcatcttag-caactgg-3' (SEQ ID NO: 47) containing an Xho I recognition sequence as primers and an RT-PCR kit (SuperScriptIII One-Step RT-PCR System with Platinum Taq DNA Polymerase (produced by Invitrogen)). The thus obtained cDNA was cleaved with Nco I and Xho I (both produced by New England Biolabs). The resultant was then incorporated into a plasmid (pET-28a(+) plasmid DNA (produced by Novagen)) that had been cleaved with Nco I and Xho I in advance using a DNA Ligation Kit (produced by BioDynamics Laboratory). In addition, pET-28a(+) contained a T7 promoter and a T7 terminator. Furthermore, pET-28a(+) contained a gene encoding a histidine tag in the vicinity of the cloning site, so that the histidine tag was added to the C-terminal side of the target protein to be expressed. Moreover, pET-28a(+) had kanamycin resistance.

Next, site-specific mutagenesis was performed using the thus obtained recombinant plasmid as a template and a Transformer site-directed mutagenesis kit (produced by Clontech). A selection primer used herein was a DNA consisting of the nucleotide sequence: 5'-gttaagccagtttacactccgc-3' (SEQ ID NO: 49) that contains a sequence differing from a restriction enzyme Bst1107 I recognition sequence in pET-28a(+) by a single nucleotide. A mutagenesis primer used herein was a DNA consisting of the nucleotide sequence: 5'-gcacaccg-gagatcttggatattatg-3' (SEQ ID NO: 55). The 5' ends of both primers had been phosphorylated in advance with T4 polynucleotide kinase (produced by TOYOBO). A recombinant plasmid was synthesized using T4 DNA polymerase and T4 DNA ligase provided with a Transformer site-directed mutagenesis kit. After cleavage treatment with Bst1107 I, recombinant plasmids that had not been cleaved with Bst1107 I were introduced into *Escherichia coli* mismatch repair deficient strain BMH71-18mutS, followed by culturing of *Escherichia coli*. The thus obtained recombinant plasmids were further cleaved with Bst1107 I, and then recombinant plasmids that had not been cleaved with Bst1107 I were selected as recombinant plasmids into which mutation had been introduced. Transformed *Escherichia coli* was prepared in a manner similar to that of Example 1 except that the thus obtained recombinant plasmid had been introduced into *Escherichia coli*. The mutant firefly luciferase was collected and then purified. In addition, the nucleotide sequence of the mutant firefly luciferase gene (DNA) in the recombinant plasmids was determined in a manner similar to that of Example 1. Thus it was confirmed that the relevant gene encoded the target mutant firefly luciferase.

Protein quantification for the thus obtained mutant firefly luciferase was performed using Bio-Rad Protein Assay (produced by BIORAD) based on the Bradford method and IgG as a standard. After addition of 50 μL of a reaction buffer containing mutant firefly luciferase (0.1 mg/mL) to a 96-well plate (LumiNunc plate produced by Nunc), 50 μL of a 50 mM Tris-HCl buffer (pH7.4)) containing a substrate buffer ($1 \times 10^{-7}$ M D-firefly luciferin (produced by Wako Pure Chemical Industries, Ltd.), $1 \times 10^{-6}$ M ATP, and 10 mM $MgCl_2$ was added using an injector provided with a microplate reader (ARVO MX produced by Perkin-Elmer). Subsequently, luminescence intensity was measured using the above microplate reader.

Also for Genji firefly luciferase (wild type), transformed *Escherichia coli* was prepared in a manner similar to that employed for the mutant firefly luciferase except that a recombinant plasmid (pET-28a(+)) obtained as described above containing Genji firefly luciferase gene (cDNA) was used instead of the recombinant plasmid containing the mutant firefly luciferase gene. The enzyme was collected and purified and then the luminescence intensity of the enzyme was measured. Subsequently, the ratio (luminescence intensity ratio) of the luminescence intensity of the mutant firefly luciferase to that of Genji firefly luciferase was found.

Example 21

A mutant firefly luciferase consisting of an amino acid sequence derived from the amino acid sequence of Genji firefly luciferase was produced as described below by substitution of aspartic acid (Asp) at position 438 with glycine (Gly). Its firefly luciferase activity (luminescence intensity) was then measured.

The purified mutant firefly luciferase was obtained and then the luminescence intensity thereof was measured in a manner similar to that of Example 20 except that a DNA consisting of the nucleotide sequence: 5'-ctttattgtcg-gtcgtttgaagtc-3' (SEQ ID NO: 56) was used as a mutagenesis primer in site-specific mutagenesis. Subsequently, the ratio (luminescence intensity ratio) of the luminescence intensity of the mutant firefly luciferase to that of Genji firefly luciferase was found using the luminescence intensity of Genji firefly luciferase measured in Example 20. Furthermore, in a manner similar to that of Example 1, the nucleotide sequence of the mutant firefly luciferase gene (DNA) in the recombinant plasmids was determined. Thus, it was confirmed that the relevant gene encoded the target mutant firefly luciferase.

Example 22

A mutant firefly luciferase consisting of an amino acid sequence derived from the amino acid sequence of Genji firefly luciferase was produced as described below by substitution of isoleucine (Ile) at position 532 with arginine (Arg). Its firefly luciferase activity (luminescence intensity) was then measured.

The purified mutant firefly luciferase was obtained and then the luminescence intensity thereof was measured in a manner similar to that of Example 20 except that a DNA consisting of the nucleotide sequence: 5'-ggtcttactggaaaaagg-gacggcagagc-3' (SEQ ID NO: 57) was used as a mutagenesis primer in site-specific mutagenesis. Subsequently, the ratio (luminescence intensity ratio) of the luminescence intensity of the mutant firefly luciferase to that of Genji firefly luciferase was found using the luminescence intensity of Genji firefly luciferase measured in Example 20. Furthermore, in a manner similar to that of Example 1, the nucleotide sequence of the mutant firefly luciferase gene (DNA) in the recombinant plasmids was determined. Thus, it was confirmed that the relevant gene encoded the target mutant firefly luciferase.

Example 23

A mutant firefly luciferase consisting of an amino acid sequence derived from the amino acid sequence of Genji firefly luciferase was produced in a manner similar to that of Example 20 by substitution of isoleucine (Ile) at position 425 with leucine (Leu). Its firefly luciferase activity (luminescence intensity) was then measured. Also for North American firefly luciferase (wild type), a purified enzyme was obtained and then and then the luminescence intensity thereof was measured in a manner similar to that of Example 1. Subsequently, the ratio (luminescence intensity ratio) of the luminescence intensity of the mutant firefly luciferase to that of North American firefly luciferase was found. Furthermore, in a manner similar to that of Example 1, the nucleotide sequence of the mutant firefly luciferase gene (DNA) in the recombinant plasmids was determined. Thus, it was confirmed that the relevant gene encoded the target mutant firefly luciferase.

Comparative Example 21

A mutant firefly luciferase consisting of an amino acid sequence derived from the amino acid sequence of Genji firefly luciferase was produced in a manner similar to that of Example 21 by substitution of aspartic acid (Asp) at position 438 with glycine (Gly). Its firefly luciferase activity (luminescence intensity) was then measured. Subsequently, the ratio (luminescence intensity ratio) of the luminescence intensity of the mutant firefly luciferase to that of North American firefly luciferase was found using the luminescence intensity of North American firefly luciferase measured in Example 23. Furthermore, in a manner similar to that of Example 1, the nucleotide sequence of the mutant firefly luciferase gene (DNA) in the recombinant plasmids was determined. Thus, it was confirmed that the relevant gene encoded the target mutant firefly luciferase.

Comparative Example 22

A mutant firefly luciferase consisting of an amino acid sequence derived from the amino acid sequence of Genji firefly luciferase was produced in a manner similar to that of Example 22 by substitution of isoleucine (Ile) at position 532 with arginine (Arg). Its firefly luciferase activity (luminescence intensity) was then measured. Subsequently, the ratio (luminescence intensity ratio) of the luminescence intensity of the mutant firefly luciferase to that of North American firefly luciferase was found using the luminescence intensity of North American firefly luciferase measured in Example 23. Furthermore, in a manner similar to that of Example 1, the nucleotide sequence of the mutant firefly luciferase gene (DNA) in the recombinant plasmids was determined. Thus, it was confirmed that the relevant gene encoded the target mutant firefly luciferase.

Table 5 shows the results of Examples 20 to 23 and Comparative examples 21 and 22. In addition, the amino acid sequence of Genji firefly luciferase and the amino acid sequence of North American firefly luciferase share 68% homology.

TABLE 5

|           |                       | Luminescence intensity (cps) | Luminescence intensity ratio |
|-----------|-----------------------|------------------------------|------------------------------|
| Wild type | Genji firefly         | 713                          | —                            |
| Mutant    | Example 20            | 3318                         | 4.7                          |
|           | Example 21            | 2517                         | 3.5                          |
|           | Example 22            | 1592                         | 2.2                          |
| Wild type | North American firefly| 2972                         | —                            |
| Mutant    | Example 23            | 3318                         | 1.1                          |
|           | Comparative example 21| 2517                         | 0.8                          |
|           | Comparative example 22| 1592                         | 0.5                          |

As is clear from Table 5, substitution of isoleucine (Ile) at position 425 with leucine (Leu), substitution of aspartic acid (Asp) at position 438 with glycine (Gly), and substitution of isoleucine (Ile) at position 532 with arginine (Arg) in the amino acid sequence of Genji firefly luciferase resulted in luminescence intensity increased to levels times, 3.5 times, and 2.2 times greater, respectively, than that of Genji firefly luciferase. It was revealed by these results that the mutant firefly luciferase consisting of a mutant amino acid sequence derived from the amino acid sequence of Genji firefly luciferase by substitution of the following substitution (a), (b), or (c) has sufficiently higher luminescence intensity than that of Genji firefly luciferase.

(a) Substitution of an amino acid at position 425 with a nonpolar amino acid having a molecular weight that is the same as or higher than that of the amino acid to be substituted.

(b) Substitution of an amino acid at position 438 with an amino acid that has a molecular weight lower than that of the amino acid to be substituted and is selected from among glycine, alanine, and serine.

(c) Substitution of an amino acid at position 532 with a positively-charged amino acid that has an isoelectric point higher than that of the amino acid to be substituted.

Furthermore, as is clear from Table 5, substitution of isoleucine (Ile) at position 425 with leucine (Leu) in the amino acid sequence of Genji firefly luciferase resulted in an increase of luminescence intensity to a level 1.1 times greater than that of North American firefly luciferase. These results revealed the presence of mutant firefly luciferases each having luminescence intensity higher than that of North American firefly luciferase among mutant firefly luciferases each consisting of a mutant amino acid sequence derived from the amino acid sequence of North American firefly luciferase by at least the above substitution (a) and having 68% homology with the amino acid sequence of North American firefly luciferase.

INDUSTRIAL APPLICABILITY

The mutant firefly luciferase of the present invention can be used for detection of extremely trace amounts of bacteria and the like in food and drink.

The invention claimed is:

1. An isolated mutant *Photinus pyralis* luciferase which has the following mutations (a), (b) and (c) in the amino acid sequence of SEQ ID NO: 1 and has a luminescence intensity higher than that of wild-type *Photinus pyralis* luciferase consisting of the amino acid sequence of SEQ ID NO: 1:

(a) substitution of isoleucine at position 423 with leucine;
(b) substitution of aspartic acid at position 436 with glycine; and
(c) substitution of leucine at position 530 with arginine.

* * * * *

SEQUENCE LISTING

<160> NUMBER OF SEQ ID NOS: 57

<210> SEQ ID NO 1
<211> LENGTH: 550
<212> TYPE: PRT
<213> ORGANISM: Photinus pyralis

<400> SEQUENCE: 1

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
                20                  25                  30

Tyr Ala Leu Val Pro Gly Thr Ile Ala Phe Thr Asp Ala His Ile Glu
            35                  40                  45

Val Asn Ile Thr Tyr Ala Glu Tyr Phe Glu Met Ser Val Arg Leu Ala
        50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

```
Ile Ile Gln Lys Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
            165                 170                 175

Asn Glu Tyr Asp Phe Val Pro Glu Ser Phe Asp Arg Asp Lys Thr Ile
        180                 185                 190

Ala Leu Ile Met Asn Ser Ser Gly Ser Thr Gly Leu Pro Lys Gly Val
    195                 200                 205

Ala Leu Pro His Arg Thr Ala Cys Val Arg Phe Ser His Ala Arg Asp
210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
530                 535                 540

Gly Gly Lys Ser Lys Leu
545                 550
```

<210> SEQ ID NO 2
<211> LENGTH: 548
<212> TYPE: PRT
<213> ORGANISM: Luciola lateralis

<400> SEQUENCE: 2

```
Met Glu Asn Met Glu Asn Asp Glu Asn Ile Val Tyr Gly Pro Glu Pro
1               5                   10                  15

Phe Tyr Pro Ile Glu Glu Gly Ser Ala Gly Ala Gln Leu Arg Lys Tyr
            20                  25                  30

Met Asp Arg Tyr Ala Lys Leu Gly Ala Ile Ala Phe Thr Asn Ala Leu
        35                  40                  45

Thr Gly Val Asp Tyr Thr Tyr Ala Glu Tyr Leu Glu Lys Ser Cys Cys
    50                  55                  60

Leu Gly Glu Ala Leu Lys Asn Tyr Gly Leu Val Val Asp Gly Arg Ile
65                  70                  75                  80

Ala Leu Cys Ser Glu Asn Cys Glu Glu Phe Ile Pro Val Leu Ala
                85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
    130                 135                 140

Val Thr Ala Ile Lys Thr Ile Val Ile Leu Asp Ser Lys Val Asp Tyr
145                 150                 155                 160

Arg Gly Tyr Gln Ser Met Asp Asn Phe Ile Lys Lys Asn Thr Pro Pro
                165                 170                 175

Gly Phe Lys Gly Ser Ser Phe Lys Thr Val Glu Val Asn Arg Lys Glu
            180                 185                 190

Gln Val Ala Leu Ile Met Asn Ser Ser Gly Ser Thr Gly Leu Pro Lys
        195                 200                 205

Gly Val Gln Leu Thr His Glu Asn Ala Val Thr Arg Phe Ser His Ala
    210                 215                 220

Arg Asp Pro Ile Tyr Gly Asn Gln Val Ser Pro Gly Thr Ala Ile Leu
225                 230                 235                 240

Thr Val Val Pro Phe His His Gly Phe Gly Met Phe Thr Thr Leu Gly
                245                 250                 255

Tyr Leu Thr Cys Gly Phe Arg Ile Val Met Leu Thr Lys Phe Asp Glu
            260                 265                 270

Glu Thr Phe Leu Lys Thr Leu Gln Asp Tyr Lys Cys Ser Ser Val Ile
        275                 280                 285

Leu Val Pro Thr Leu Phe Ala Ile Leu Asn Arg Ser Glu Leu Leu Asp
    290                 295                 300

Lys Tyr Asp Leu Ser Asn Leu Val Glu Ile Ala Ser Gly Gly Ala Pro
305                 310                 315                 320

Leu Ser Lys Glu Ile Gly Glu Ala Val Ala Arg Arg Phe Asn Leu Pro
                325                 330                 335

Gly Val Arg Gln Gly Tyr Gly Leu Thr Glu Thr Thr Ser Ala Ile Ile
            340                 345                 350

Ile Thr Pro Glu Gly Asp Asp Lys Pro Gly Ala Ser Gly Lys Val Val
        355                 360                 365

Pro Leu Phe Lys Ala Lys Val Ile Asp Leu Asp Thr Lys Lys Thr Leu
    370                 375                 380
```

```
Gly Pro Asn Arg Arg Gly Glu Val Cys Val Lys Gly Pro Met Leu Met
385                 390                 395                 400

Lys Gly Tyr Val Asp Asn Pro Glu Ala Thr Arg Glu Ile Ile Asp Glu
            405                 410                 415

Glu Gly Trp Leu His Thr Gly Asp Ile Gly Tyr Tyr Asp Glu Glu Lys
        420                 425                 430

His Phe Phe Ile Val Asp Arg Leu Lys Ser Leu Ile Lys Tyr Lys Gly
    435                 440                 445

Tyr Gln Val Pro Pro Ala Glu Leu Glu Ser Val Leu Leu Gln His Pro
450                 455                 460

Asn Ile Phe Asp Ala Gly Val Ala Gly Val Pro Asp Pro Ile Ala Gly
465                 470                 475                 480

Glu Leu Pro Gly Ala Val Val Val Leu Glu Lys Gly Lys Ser Met Thr
                485                 490                 495

Glu Lys Glu Val Met Asp Tyr Val Ala Ser Gln Val Ser Asn Ala Lys
            500                 505                 510

Arg Leu Arg Gly Gly Val Arg Phe Val Asp Glu Val Pro Lys Gly Leu
        515                 520                 525

Thr Gly Lys Ile Asp Gly Lys Ala Ile Arg Glu Ile Leu Lys Lys Pro
    530                 535                 540

Val Ala Lys Met
545

<210> SEQ ID NO 3
<211> LENGTH: 548
<212> TYPE: PRT
<213> ORGANISM: Luciola cruciata

<400> SEQUENCE: 3

Met Glu Asn Met Glu Asn Asp Glu Asn Ile Val Val Gly Pro Lys Pro
1               5                   10                  15

Phe Tyr Pro Ile Glu Glu Gly Ser Ala Gly Thr Gln Leu Arg Lys Tyr
            20                  25                  30

Met Glu Arg Tyr Ala Lys Leu Gly Ala Ile Ala Phe Thr Asn Ala Val
        35                  40                  45

Thr Gly Val Asp Tyr Ser Tyr Ala Glu Tyr Leu Glu Lys Ser Cys Cys
    50                  55                  60

Leu Gly Lys Ala Leu Gln Asn Tyr Gly Leu Val Val Asp Gly Arg Ile
65                  70                  75                  80

Ala Leu Cys Ser Glu Asn Cys Glu Glu Phe Phe Ile Pro Val Ile Ala
                85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
    130                 135                 140

Val Thr Thr Ile Lys Thr Ile Val Ile Leu Asp Ser Lys Val Asp Tyr
145                 150                 155                 160

Arg Gly Tyr Gln Cys Leu Asp Thr Phe Ile Lys Arg Asn Thr Pro Pro
                165                 170                 175

Gly Phe Gln Ala Ser Ser Phe Lys Thr Val Glu Val Asp Arg Lys Glu
            180                 185                 190

Gln Val Ala Leu Ile Met Asn Ser Ser Gly Ser Thr Gly Leu Pro Lys
        195                 200                 205
```

Gly Val Gln Leu Thr His Glu Asn Thr Val Thr Arg Phe Ser His Ala
            210                 215                 220

Arg Asp Pro Ile Tyr Gly Asn Gln Val Ser Pro Gly Thr Ala Val Leu
225                 230                 235                 240

Thr Val Val Pro Phe His His Gly Phe Gly Met Phe Thr Thr Leu Gly
            245                 250                 255

Tyr Leu Ile Cys Gly Phe Arg Val Val Met Leu Thr Lys Phe Asp Glu
            260                 265                 270

Glu Thr Phe Leu Lys Thr Leu Gln Asp Tyr Lys Cys Thr Ser Val Ile
            275                 280                 285

Leu Val Pro Thr Leu Phe Ala Ile Leu Asn Lys Ser Glu Leu Leu Asn
            290                 295                 300

Lys Tyr Asp Leu Ser Asn Leu Val Glu Ile Ala Ser Gly Gly Ala Pro
305                 310                 315                 320

Leu Ser Lys Glu Val Gly Glu Ala Val Ala Arg Arg Phe Asn Leu Pro
            325                 330                 335

Gly Val Arg Gln Gly Tyr Gly Leu Thr Glu Thr Thr Ser Ala Ile Ile
            340                 345                 350

Ile Thr Pro Glu Gly Asp Asp Lys Pro Gly Ala Ser Gly Lys Val Val
            355                 360                 365

Pro Leu Phe Lys Ala Lys Val Ile Asp Leu Asp Thr Lys Lys Ser Leu
370                 375                 380

Gly Pro Asn Arg Arg Gly Glu Val Cys Val Lys Gly Pro Met Leu Met
385                 390                 395                 400

Lys Gly Tyr Val Asn Asn Pro Glu Ala Thr Lys Glu Leu Ile Asp Glu
            405                 410                 415

Glu Gly Trp Leu His Thr Gly Asp Ile Gly Tyr Tyr Asp Glu Glu Lys
            420                 425                 430

His Phe Phe Ile Val Asp Arg Leu Lys Ser Leu Ile Lys Tyr Lys Gly
            435                 440                 445

Tyr Gln Val Pro Pro Ala Glu Leu Glu Ser Val Leu Leu Gln His Pro
450                 455                 460

Ser Ile Phe Asp Ala Gly Val Ala Gly Val Pro Asp Pro Val Ala Gly
465                 470                 475                 480

Glu Leu Pro Gly Ala Val Val Val Leu Glu Ser Gly Lys Asn Met Thr
            485                 490                 495

Glu Lys Glu Val Met Asp Tyr Val Ala Ser Gln Val Ser Asn Ala Lys
            500                 505                 510

Arg Leu Arg Gly Gly Val Arg Phe Val Asp Glu Val Pro Lys Gly Leu
            515                 520                 525

Thr Gly Lys Ile Asp Gly Arg Ala Ile Arg Glu Ile Leu Lys Lys Pro
            530                 535                 540

Val Ala Lys Met
545

<210> SEQ ID NO 4
<211> LENGTH: 1650
<212> TYPE: DNA
<213> ORGANISM: Photinus pyralis

<400> SEQUENCE: 4
atggaagacg ccaaaaacat aaagaaaggc ccggcgccat tctatcctct agaggatgga     60
accgctggag agcaactgca taaggctatg aagagatacg ccctggttcc cggaacaatt    120
gcttttacag atgcacatat cgaggtgaac atcacgtacg cggaatactt cgaaatgtcc    180

```
gttcggttgg cagaagctat gaaacgatat gggctgaata caaatcacag aatcgtcgta      240
tgcagtgaaa actctcttca attctttatg ccggtgttgg gcgcgttatt tatcggagtt      300
gcagttgcgc ccgcgaacga catttataat gaacgtgaat tgctcaacag tatgaacatt      360
tcgcagccta ccgtagtgtt tgtttccaaa aaggggttgc aaaaaatttt gaacgtgcaa      420
aaaaaattac caataatcca gaaaattatt atcatggatt ctaaaacgga ttaccaggga      480
tttcagtcga tgtacacgtt cgtcacatct catctaccct ccggttttaa tgaatacgat      540
tttgtaccag agtcctttga tcgtgacaaa acaattgcac tgataatgaa ttcctctgga      600
tctactgggt tacctaaggg tgtggccctt ccgcatagaa ctgcctgcgt cagattctcg      660
catgccagag atcctatttt tggcaatcaa atcattccgg atactgcgat tttaagtgtt      720
gttccattcc atcacggttt tggaatgttt actacactcg atatttgat atgtggattt      780 cgagtcgtct taatgtatag atttgaagaa gagctgtttt tacgatccct tcaggattac      840
aaaattcaaa gtgcgttgct agtaccaacc ctatttcat tcttcgccaa aagcactctg      900
attgacaaat acgatttatc taatttacac gaaattgctt ctgggggcgc acctctttcg      960
aaagaagtcg gggaagcggt tgcaaaacgc ttccatcttc cagggatacg acaaggatat     1020
gggctcactg agactacatc agctattctg attacacccg aggggatga taaaccgggc     1080 gcggtcggta agttgttcc attttttgaa gcgaaggttg tggatctgga tacccggaaa     1140
acgctgggcg ttaatcagag aggcgaatta tgtgtcagag acctatgat tatgtccggt     1200 tatgtaaaca atccggaagc gaccaacgcc ttgattgaca aggatggatg gctacattct     1260
ggagacatag cttactggga cgaagacgaa cacttcttca tagttgaccg cttgaagtct     1320
ttaattaaat acaaaggata tcaggtggcc ccgctgaat tggaatcgat attgttacaa     1380 cacccccaaca tcttcgacgc gggcgtggca ggtcttcccg acgatgacgc cggtgaactt     1440
cccgccgccg ttgttgtttt ggagcacgga aagacgatga cggaaaaaga gatcgtggat     1500
tacgtcgcca gtcaagtaac aaccgcgaaa aagttgcgcg gaggagttgt gtttgtggac     1560
gaagtaccga aaggtcttac cggaaaaactc gacgcaagaa aaatcagaga gatcctcata     1620
aaggccaaga agggcggaaa gtccaaattg                                      1650
```

<210> SEQ ID NO 5
<211> LENGTH: 24
<212> TYPE: DNA
<213> ORGANISM: Artificial Sequence
<220> FEATURE:
<223> OTHER INFORMATION: Synthetic Construct

<400> SEQUENCE: 5

```
gactccatgg aagacgccaa aaac                                              24
```

<210> SEQ ID NO 6
<211> LENGTH: 28
<212> TYPE: DNA
<213> ORGANISM: Artificial Sequence
<220> FEATURE:
<223> OTHER INFORMATION: Synthetic Construct

<400> SEQUENCE: 6

```
gacactcgag caatttggac tttccgcc                                          28
```

<210> SEQ ID NO 7
<211> LENGTH: 21
<212> TYPE: DNA
<213> ORGANISM: Artificial Sequence

```
<220> FEATURE:
<223> OTHER INFORMATION: Synthetic Construct

<400> SEQUENCE: 7
cacgatcatg agcacccgtg g                                              21

<210> SEQ ID NO 8
<211> LENGTH: 33
<212> TYPE: DNA
<213> ORGANISM: Artificial Sequence
<220> FEATURE:
<223> OTHER INFORMATION: Synthetic Construct

<400> SEQUENCE: 8
ggctacattc tggagactta gcttactggg acg                                 33

<210> SEQ ID NO 9
<211> LENGTH: 1650
<212> TYPE: DNA
<213> ORGANISM: Photinus pyralis

<400> SEQUENCE: 9
atggaagacg ccaaaaacat aaagaaaggc ccggcgccat tctatcctct agaggatgga     60
accgctggag agcaactgca taaggctatg aagagatacg ccctggttcc cggaacaatt    120
gcttttacag atgcacatat cgaggtgaac atcacgtacg cggaatactt cgaaatgtcc    180
gttcggttgg cagaagctat gaaacgatat gggctgaata caaatcacag aatcgtcgta    240
tgcagtgaaa actctcttca attctttatg ccggtgttgg gcgcgttatt tatcggagtt    300
gcagttgcgc ccgcgaacga catttataat gaacgtgaat tgctcaacag tatgaacatt    360
tcgcagccta ccgtagtgtt tgtttccaaa aaggggttgc aaaaaatttt gaacgtgcaa    420
aaaaaattac caataatcca gaaaattatt atcatggatt ctaaaacgga ttaccaggga    480
tttcagtcga tgtacacgtt cgtcacatct catctacctc ccggttttaa tgaatacgat    540
tttgtaccag agtcctttga tcgtgacaaa acaattgcac tgataatgaa ttcctctgga    600
tctactgggt tacctaaggg tgtggcccct tccgcatagaa ctgcctgcgt cagattctcg    660
catgccagag atcctatttt tggcaatcaa atcattccgg atactgcgat tttaagtgtt    720
gttccattcc atcacggttt tggaatgttt actacactcg gatatttgat atgtggattt    780
cgagtcgtct taatgtatag atttgaagaa gagctgtttt tacgatccct tcaggattac    840
aaaattcaaa gtgcgttgct agtaccaacc ctatttttcat tcttcgccaa aagcactctg    900
attgacaaat acgatttatc taatttacac gaaattgctt ctgggggcgc acctctttcg    960
aaagaagtcg gggaagcggt tgcaaaacgc ttccatcttc cagggatacg acaaggatat   1020
gggctcactg agactacatc agctattctg attacacccg agggggatga taaaccgggc   1080
gcggtcggta agttgttcc attttttgaa gcgaaggttg tggatctgga taccgggaaa   1140
acgctgggcg ttaatcagag aggcgaatta tgtgtcagag gacctatgat tatgtccggt   1200
tatgtaaaca atccggaagc gaccaacgcc ttgattgaca aggatggatg gctacattct   1260
ggagacttag cttactggga cgaagacgaa cacttcttca tagttgaccg cttgaagtct   1320
ttaattaaat acaaaggata tcaggtggcc cccgctgaat tggaatcgat attgttacaa   1380 cacccccaaca tcttcgacgc gggcgtggca ggtcttcccg acgatgacgc cggtgaactt   1440
cccgccgccg ttgttgtttt ggagcacgga aagacgatga cggaaaaaga tcgtgtggat   1500
tacgtcgcca gtcaagtaac aaccgcgaaa aagttgcgcg gaggagttgt gtttgtggac   1560
```

```
gaagtaccga aaggtcttac cggaaaactc gacgcaagaa aaatcagaga gatcctcata    1620
aaggccaaga agggcggaaa gtccaaattg                                     1650

<210> SEQ ID NO 10
<211> LENGTH: 33
<212> TYPE: DNA
<213> ORGANISM: Artificial Sequence
<220> FEATURE:
<223> OTHER INFORMATION: Synthetic Construct

<400> SEQUENCE: 10
ggctacattc tggagacatg gcttactggg acg                                 33

<210> SEQ ID NO 11
<211> LENGTH: 33
<212> TYPE: DNA
<213> ORGANISM: Artificial Sequence
<220> FEATURE:
<223> OTHER INFORMATION: Synthetic Construct

<400> SEQUENCE: 11
ggctacattc tggagacttt gcttactggg acg                                 33

<210> SEQ ID NO 12
<211> LENGTH: 33
<212> TYPE: DNA
<213> ORGANISM: Artificial Sequence
<220> FEATURE:
<223> OTHER INFORMATION: Synthetic Construct

<400> SEQUENCE: 12
ggctacattc tggagacgta gcttactggg acg                                 33

<210> SEQ ID NO 13
<211> LENGTH: 33
<212> TYPE: DNA
<213> ORGANISM: Artificial Sequence
<220> FEATURE:
<223> OTHER INFORMATION: Synthetic Construct

<400> SEQUENCE: 13
ggctacattc tggagacgca gcttactggg acg                                 33

<210> SEQ ID NO 14
<211> LENGTH: 33
<212> TYPE: DNA
<213> ORGANISM: Artificial Sequence
<220> FEATURE:
<223> OTHER INFORMATION: Synthetic Construct

<400> SEQUENCE: 14
ggctacattc tggagacgga gcttactggg acg                                 33

<210> SEQ ID NO 15
<211> LENGTH: 33
<212> TYPE: DNA
<213> ORGANISM: Artificial Sequence
<220> FEATURE:
<223> OTHER INFORMATION: Synthetic Construct

<400> SEQUENCE: 15
ggctacattc tggagactca gcttactggg acg                                 33

<210> SEQ ID NO 16
<211> LENGTH: 33
```

```
<212> TYPE: DNA
<213> ORGANISM: Artificial Sequence
<220> FEATURE:
<223> OTHER INFORMATION: Synthetic Construct

<400> SEQUENCE: 16
ggctacattc tggagaccaa gcttactggg acg                                    33

<210> SEQ ID NO 17
<211> LENGTH: 33
<212> TYPE: DNA
<213> ORGANISM: Artificial Sequence
<220> FEATURE:
<223> OTHER INFORMATION: Synthetic Construct

<400> SEQUENCE: 17
ggctacattc tggagacaga gcttactggg acg                                    33

<210> SEQ ID NO 18
<211> LENGTH: 33
<212> TYPE: DNA
<213> ORGANISM: Artificial Sequence
<220> FEATURE:
<223> OTHER INFORMATION: Synthetic Construct

<400> SEQUENCE: 18
ggctacattc tggagacaaa gcttactggg acg                                    33

<210> SEQ ID NO 19
<211> LENGTH: 33
<212> TYPE: DNA
<213> ORGANISM: Artificial Sequence
<220> FEATURE:
<223> OTHER INFORMATION: Synthetic Construct

<400> SEQUENCE: 19
ggctacattc tggagacgaa gcttactggg acg                                    33

<210> SEQ ID NO 20
<211> LENGTH: 29
<212> TYPE: DNA
<213> ORGANISM: Artificial Sequence
<220> FEATURE:
<223> OTHER INFORMATION: Synthetic Construct

<400> SEQUENCE: 20
cacttcttca tagttggccg cttgaagtc                                         29

<210> SEQ ID NO 21
<211> LENGTH: 29
<212> TYPE: DNA
<213> ORGANISM: Artificial Sequence
<220> FEATURE:
<223> OTHER INFORMATION: Synthetic Construct

<400> SEQUENCE: 21
cacttcttca tagttgcccg cttgaagtc                                         29

<210> SEQ ID NO 22
<211> LENGTH: 29
<212> TYPE: DNA
<213> ORGANISM: Artificial Sequence
<220> FEATURE:
<223> OTHER INFORMATION: Synthetic Construct

<400> SEQUENCE: 22
cacttcttca tagttagccg cttgaagtc                                         29
```

<210> SEQ ID NO 23
<211> LENGTH: 29
<212> TYPE: DNA
<213> ORGANISM: Artificial Sequence
<220> FEATURE:
<223> OTHER INFORMATION: Synthetic Construct

<400> SEQUENCE: 23
cacttcttca tagttaaccg cttgaagtc                              29

<210> SEQ ID NO 24
<211> LENGTH: 29
<212> TYPE: DNA
<213> ORGANISM: Artificial Sequence
<220> FEATURE:
<223> OTHER INFORMATION: Synthetic Construct

<400> SEQUENCE: 24
cacttcttca tagttgaacg cttgaagtc                              29

<210> SEQ ID NO 25
<211> LENGTH: 29
<212> TYPE: DNA
<213> ORGANISM: Artificial Sequence
<220> FEATURE:
<223> OTHER INFORMATION: Synthetic Construct

<400> SEQUENCE: 25
cacttcttca tagttgtccg cttgaagtc                              29

<210> SEQ ID NO 26
<211> LENGTH: 19
<212> TYPE: DNA
<213> ORGANISM: Artificial Sequence
<220> FEATURE:
<223> OTHER INFORMATION: Synthetic Construct

<400> SEQUENCE: 26
ccggaaaacg cgacgcaag                                         19

<210> SEQ ID NO 27
<211> LENGTH: 26
<212> TYPE: DNA
<213> ORGANISM: Artificial Sequence
<220> FEATURE:
<223> OTHER INFORMATION: Synthetic Construct

<400> SEQUENCE: 27
ggtcttaccg gaaaaaagga cgcaag                                 26

<210> SEQ ID NO 28
<211> LENGTH: 19
<212> TYPE: DNA
<213> ORGANISM: Artificial Sequence
<220> FEATURE:
<223> OTHER INFORMATION: Synthetic Construct

<400> SEQUENCE: 28
ccggaaaaca cgacgcaag                                         19

<210> SEQ ID NO 29
<211> LENGTH: 26
<212> TYPE: DNA
<213> ORGANISM: Artificial Sequence
<220> FEATURE:

<223> OTHER INFORMATION: Synthetic Construct

<400> SEQUENCE: 29
ggtcttaccg gaaaagtcga cgcaag                                            26

<210> SEQ ID NO 30
<211> LENGTH: 26
<212> TYPE: DNA
<213> ORGANISM: Artificial Sequence
<220> FEATURE:
<223> OTHER INFORMATION: Synthetic Construct

<400> SEQUENCE: 30
ggtcttaccg gaaaaatcga cgcaag                                            26

<210> SEQ ID NO 31
<211> LENGTH: 26
<212> TYPE: DNA
<213> ORGANISM: Artificial Sequence
<220> FEATURE:
<223> OTHER INFORMATION: Synthetic Construct

<400> SEQUENCE: 31
ggtcttaccg gaaaagccga cgcaag                                            26

<210> SEQ ID NO 32
<211> LENGTH: 26
<212> TYPE: DNA
<213> ORGANISM: Artificial Sequence
<220> FEATURE:
<223> OTHER INFORMATION: Synthetic Construct

<400> SEQUENCE: 32
ggtcttaccg gaaaacccga cgcaag                                            26

<210> SEQ ID NO 33
<211> LENGTH: 26
<212> TYPE: DNA
<213> ORGANISM: Artificial Sequence
<220> FEATURE:
<223> OTHER INFORMATION: Synthetic Construct

<400> SEQUENCE: 33
ggtcttaccg gaaaattcga cgcaag                                            26

<210> SEQ ID NO 34
<211> LENGTH: 26
<212> TYPE: DNA
<213> ORGANISM: Artificial Sequence
<220> FEATURE:
<223> OTHER INFORMATION: Synthetic Construct

<400> SEQUENCE: 34
ggtcttaccg gaaaagacga cgcaag                                            26

<210> SEQ ID NO 35
<211> LENGTH: 26
<212> TYPE: DNA
<213> ORGANISM: Artificial Sequence
<220> FEATURE:
<223> OTHER INFORMATION: Synthetic Construct

<400> SEQUENCE: 35
ggtcttaccg gaaaaagcga cgcaag                                            26

<210> SEQ ID NO 36

```
<211> LENGTH: 26
<212> TYPE: DNA
<213> ORGANISM: Artificial Sequence
<220> FEATURE:
<223> OTHER INFORMATION: Synthetic Construct

<400> SEQUENCE: 36
ggtcttaccg gaaaatacga cgcaag                                          26

<210> SEQ ID NO 37
<211> LENGTH: 1650
<212> TYPE: DNA
<213> ORGANISM: Photinus pyralis

<400> SEQUENCE: 37
atggaagacg ccaaaaacat aaagaaaggc ccggcgccat tctatcctct agaggatgga      60
accgctggag agcaactgca taaggctatg aagagatacg ccctggttcc cggaacaatt     120
gcttttacag atgcacatat cgaggtgaac atcacgtacg cggaatactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgaacatt     360
tcgcagccta ccgtagtgtt tgtttccaaa aaggggttgc aaaaaatttt gaacgtgcaa     420
aaaaaattac caataatcca gaaaattatt atcatggatt ctaaaacgga ttaccaggga     480
tttcagtcga tgtacacgtt cgtcacatct catctacctc ccggttttaa tgaatacgat     540
tttgtaccag agtcctttga tcgtgacaaa acaattgcac tgataatgaa ttcctctgga     600
tctactgggt tacctaaggg tgtggcccct ccgcatagaa ctgcctgcgt cagattctcg     660
catgccagag atcctatttt tggcaatcaa atcattccgg atactgcgat tttaagtgtt     720
gttccattcc atcacggttt tggaatgttt actacactcg gatatttgat atgtggattt     780
cgagtcgtct taatgtatag atttgaagaa gagctgtttt tacgatccct tcaggattac     840
aaaattcaaa gtgcgttgct agtaccaacc ctattttcat tcttcgccaa aagcactctg     900
attgacaaat acgatttatc taatttacac gaaattgctt ctgggggcgc acctctttcg     960
aaagaagtcg ggaagcggt tgcaaaacgc ttccatcttc cagggatacg acaaggatat    1020
gggctcactg agactacatc agctattctg attacacccg agggggatga taaaccgggc    1080
gcggtcggta agttgttcc atttttgaa gcgaaggttg tggatctgga taccgggaaa    1140
acgctgggcg ttaatcagag aggcgaatta tgtgtcagag acctatgat tatgtccggt    1200
tatgtaaaca atccggaagc gaccaacgcc ttgattgaca aggatggatg gctacattct    1260
ggagacttag cttactggga cgaagacgaa cacttcttca tagttgaccg cttgaagtct    1320
ttaattaaat acaaaggata tcaggtggcc cccgctgaat tggaatcgat attgttacaa    1380
cacccccaaca tcttcgacgc gggcgtggca ggtcttcccg acgatgacgc cggtgaactt    1440
cccgccgccg ttgttgtttt ggagcacgga aagacgatga cggaaaaaga gatcgtggat    1500
tacgtcgcca gtcaagtaac aaccgcgaaa aagttgcgcg gaggagttgt gtttgtggac    1560
gaagtaccga aaggtcttac cggaaaacgc gacgcaagaa aaatcagaga gatcctcata    1620
aaggccaaga agggcggaaa gtccaaattg                                    1650

<210> SEQ ID NO 38
<211> LENGTH: 1650
<212> TYPE: DNA
<213> ORGANISM: Photinus pyralis
```

<400> SEQUENCE: 38

```
atggaagacg ccaaaaacat aaagaaaggc ccggcgccat tctatcctct agaggatgga       60
accgctggag agcaactgca taaggctatg aagagatacg ccctggttcc cggaacaatt      120
gcttttacag atgcacatat cgaggtgaac atcacgtacg cggaatactt cgaaatgtcc      180
gttcggttgg cagaagctat gaaacgatat gggctgaata caaatcacag aatcgtcgta      240
tgcagtgaaa actctcttca attctttatg ccggtgttgg cgcgttatt tatcggagtt       300 gcagttgcgc ccgcgaacga catttataat gaacgtgaat tgctcaacag tatgaacatt      360
tcgcagccta ccgtagtgtt tgtttccaaa aaggggttgc aaaaaatttt gaacgtgcaa      420
aaaaaattac caataatcca gaaaattatt atcatggatt ctaaaacgga ttaccaggga      480
tttcagtcga tgtacacgtt cgtcacatct catctacctc ccggttttaa tgaatacgat      540
tttgtaccag agtcctttga tcgtgacaaa acaattgcac tgataatgaa ttcctctgga      600
tctactgggt tacctaaggg tgtggccctt ccgcatagaa ctgcctgcgt cagattctcg      660
catgccagag atcctatttt tggcaatcaa atcattccgg atactgcgat tttaagtgtt      720
gttccattcc atcacggttt tggaatgttt actacactcg atatttgat atgtggattt       780 cgagtcgtct taatgtatag atttgaagaa gagctgtttt tacgatccct tcaggattac      840
aaaattcaaa gtgcgttgct agtaccaacc ctatttttcat tcttcgccaa aagcactctg     900
attgacaaat acgatttatc taatttacac gaaattgctt ctgggggcgc acctctttcg      960
aaagaagtcg gggaagcggt tgcaaaacgc ttccatcttc cagggatacg acaaggatat     1020
gggctcactg agactacatc agctattctg attacacccg aggggatga taaaccgggc      1080 gcggtcggta agttgttcc atttttgaa gcgaaggttg tggatctgga taccgggaaa       1140
acgctgggcg ttaatcagag aggcgaatta tgtgtcagag gacctatgat tatgtccggt      1200
tatgtaaaca atccggaagc gaccaacgcc ttgattgaca aggatggatg ctacattct       1260 ggagacttag cttactggga cgaagacgaa cacttcttca tagttggccg cttgaagtct     1320
ttaattaaat acaaaggata tcaggtggcc cccgctgaat ggaatcgat attgttacaa       1380 cacccccaaca tcttcgacgc gggcgtggca ggtcttcccg acgatgacgc cggtgaactt     1440
cccgccgccg ttgttgtttt ggagcacgga aagacgatga cggaaaaaga gatcgtggat     1500
tacgtcgcca gtcaagtaac aaccgcgaaa aagttgcgcg gaggagttgt gtttgtggac     1560
gaagtaccga aggtcttac cggaaaactc gacgcaagaa aaatcagaga gatcctcata     1620
aaggccaaga agggcggaaa gtccaaattg                                       1650
```

<210> SEQ ID NO 39
<211> LENGTH: 1650
<212> TYPE: DNA
<213> ORGANISM: Photinus pyralis

<400> SEQUENCE: 39

```
atggaagacg ccaaaaacat aaagaaaggc ccggcgccat tctatcctct agaggatgga       60
accgctggag agcaactgca taaggctatg aagagatacg ccctggttcc tggaacaatt      120
gcttttacag atgcacatat cgaggtgaac atcacgtacg cggaatactt cgaaatgtcc      180
gttcggttgg cagaagctat gaaacgatat gggctgaata caaatcacag aatcgtcgta      240
tgcagtgaaa actctcttca attctttatg ccggtgttgg cgcgttatt tatcggagtt       300 gcagttgcgc ccgcgaacga catttataat gaacgtgaat tgctcaacag tatgaacatt      360
tcgcagccta ccgtagtgtt tgtttccaaa aaggggttgc aaaaaatttt gaacgtgcaa      420
```

```
aaaaaattac caataatcca gaaaattatt atcatggatt ctaaaacgga ttaccaggga      480
tttcagtcga tgtacacgtt cgtcacatct catctacctc ccggttttaa tgaatacgat      540
tttgtaccag agtcctttga tcgtgacaaa acaattgcac tgataatgaa ttcctctgga      600
tctactgggt tacctaaggg tgtggcccct ccgcatagaa ctgcctgcgt cagattctcg      660
catgccagag atcctatttt tggcaatcaa atcattccgg atactgcgat tttaagtgtt      720
gttccattcc atcacggttt tggaatgttt actacactcg atatttgat atgtggattt       780 cgagtcgtct taatgtatag atttgaagaa gagctgtttt tacgatccct tcaggattac      840
aaaattcaaa gtgcgttgct agtaccaacc ctatttcat tcttcgccaa aagcactctg       900
attgacaaat acgatttatc taatttacac gaaattgctt ctgggggcgc acctctttcg      960
aaagaagtcg gggaagcggt tgcaaaacgc ttccatcttc cagggatacg acaaggatat     1020
gggctcactg agactacatc agctattctg attacacccg aggggatga taaaccgggc      1080 gcggtcggta agttgttcc atttttgaa gcgaaggttg tggatctgga taccgggaaa       1140
acgctgggcg ttaatcagag aggcgaatta tgtgtcagag acctatgat tatgtccggt      1200 tatgtaaaca atccggaagc gaccaacgcc ttgattgaca aggatggatg ctacattct      1260 ggagacatag cttactggga cgaagacgaa cacttcttca tagttggccg cttgaagtct     1320
ttaattaaat acaaaggata tcaggtggcc ccgctgaat tggaatcgat attgttacaa      1380 cacccccaaca tcttcgacgc gggcgtggca ggtcttcccg acgatgacgc cggtgaactt     1440
cccgccgccg ttgttgtttt ggagcacgga agacgatga cggaaaaaga gatcgtggat      1500
tacgtcgcca gtcaagtaac aaccgcgaaa aagttgcgcg gaggagttgt gtttgtggac     1560
gaagtaccga aaggtcttac cggaaaacgc gacgcaagaa aaatcagaga gatcctcata     1620
aaggccaaga agggcggaaa gtccaaattg                                      1650
```

<210> SEQ ID NO 40
<211> LENGTH: 1650
<212> TYPE: DNA
<213> ORGANISM: Photinus pyralis

<400> SEQUENCE: 40

```
atggaagacg ccaaaaacat aaagaaaggc ccggcgccat tctatcctct agaggatgga      60
accgctggag agcaactgca taaggctatg aagagatacg ccctggttcc tggaacaatt     120
gcttttacag atgcacatat cgaggtgaac atcacgtacg cggaatactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgaacatt     360
tcgcagccta ccgtagtgtt tgtttccaaa aaggggttgc aaaaaatttt gaacgtgcaa     420
aaaaaattac caataatcca gaaaattatt atcatggatt ctaaaacgga ttaccaggga     480
tttcagtcga tgtacacgtt cgtcacatct catctacctc ccggttttaa tgaatacgat     540
tttgtaccag agtcctttga tcgtgacaaa acaattgcac tgataatgaa ttcctctgga     600
tctactgggt tacctaaggg tgtggcccct ccgcatagaa ctgcctgcgt cagattctcg     660
catgccagag atcctatttt tggcaatcaa atcattccgg atactgcgat tttaagtgtt     720
gttccattcc atcacggttt tggaatgttt actacactcg atatttgat atgtggattt      780 cgagtcgtct taatgtatag atttgaagaa gagctgtttt tacgatccct tcaggattac     840
aaaattcaaa gtgcgttgct agtaccaacc ctatttcat tcttcgccaa aagcactctg      900
```

```
attgacaaat acgatttatc taatttacac gaaattgctt ctgggggcgc acctctttcg    960
aaagaagtcg gggaagcggt tgcaaaacgc ttccatcttc cagggatacg acaaggatat   1020
gggctcactg agactacatc agctattctg attacacccg aggggatga taaaccgggc    1080 gcggtcggta agttgttcc atttttgaa gcgaaggttg tggatctgga taccgggaaa     1140
acgctgggcg ttaatcagag aggcgaatta tgtgtcagag gacctatgat tatgtccggt   1200
tatgtaaaca atccggaagc gaccaacgcc ttgattgaca aggatggatg ctacattct    1260 ggagacttag cttactggga cgaagacgaa cacttcttca tagttggccg cttgaagtct   1320
ttaattaaat acaaggata tcaggtggcc cccgctgaat tggaatcgat attgttacaa    1380
caccccaaca tcttcgacgc gggcgtggca ggtcttcccg acgatgacgc cggtgaactt   1440
cccgccgccg ttgttgtttt ggagcacgga agacgatga cggaaaaaga gatcgtggat    1500
tacgtcgcca gtcaagtaac aaccgcgaaa aagttgcgcg gaggagttgt gtttgtggac   1560
gaagtaccga aggtcttac cggaaaacgc gacgcaagaa aaatcagaga gatcctcata    1620
aaggccaaga agggcggaaa gtccaaattg                                    1650
```

<210> SEQ ID NO 41
<211> LENGTH: 21
<212> TYPE: DNA
<213> ORGANISM: Artificial Sequence
<220> FEATURE:
<223> OTHER INFORMATION: Synthetic Construct

<400> SEQUENCE: 41

```
gatgcacata ccgaggtgaa c                                               21
```

<210> SEQ ID NO 42
<211> LENGTH: 27
<212> TYPE: DNA
<213> ORGANISM: Artificial Sequence
<220> FEATURE:
<223> OTHER INFORMATION: Synthetic Construct

<400> SEQUENCE: 42

```
catatcgagg tgagcatcac gtacgcg                                         27
```

<210> SEQ ID NO 43
<211> LENGTH: 27
<212> TYPE: DNA
<213> ORGANISM: Artificial Sequence
<220> FEATURE:
<223> OTHER INFORMATION: Synthetic Construct

<400> SEQUENCE: 43

```
gcggaatact tcgaaacgtc cgttcgg                                         27
```

<210> SEQ ID NO 44
<211> LENGTH: 20
<212> TYPE: DNA
<213> ORGANISM: Artificial Sequence
<220> FEATURE:
<223> OTHER INFORMATION: Synthetic Construct

<400> SEQUENCE: 44

```
ggaatgttta cttcactcgg                                                 20
```

<210> SEQ ID NO 45
<211> LENGTH: 1650
<212> TYPE: DNA
<213> ORGANISM: Photinus pyralis

<400> SEQUENCE: 45

```
atggaagacg ccaaaaacat aaagaaaggc ccggcgccat tctatcctct agaggatgga      60
accgctggag agcaactgca taaggctatg aagagatacg ccctggttcc tggaacaatt     120
gcttttacag atgcacatac cgaggtgagc atcacgtacg cggaatactt cgaaacgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgaacatt     360
tcgcagccta ccgtagtgtt tgtttccaaa aaggggttgc aaaaaatttt gaacgtgcaa     420
aaaaaattac caataatcca gaaaattatt atcatggatt ctaaaacgga ttaccaggga     480
tttcagtcga tgtacacgtt cgtcacatct catctacctc ccggttttaa tgaatacgat     540
tttgtaccag agtcctttga tcgtgacaaa acaattgcac tgataatgaa ttcctctgga     600
tctactgggt tacctaaggg tgtggccctt ccgcatagaa ctgcctgcgt cagattctcg     660
catgccagag atcctatttt tggcaatcaa atcattccgg atactgcgat tttaagtgtt     720
gttccattcc atcacggttt tggaatgttt acttcactcg atatttgat atgtggattt     780
cgagtcgtct taatgtatag atttgaagaa gagctgtttt tacgatccct tcaggattac     840
aaaattcaaa gtgcgttgct agtaccaacc ctattttcat tcttcgccaa aagcactctg     900
attgacaaat acgatttatc taatttacac gaaattgctt ctgggggcgc acctctttcg     960
aaagaagtcg gggaagcggt tgcaaaacgc ttccatcttc cagggatacg acaaggatat    1020
gggctcactg agactacatc agctattctg attacacccg agggggatga taaaccgggc    1080
gcggtcggta agttgttcc atttttgaa gcgaaggttg tggatctgga taccgggaaa    1140
acgctgggcg ttaatcagag aggcgaatta tgtgtcagag gacctatgat tatgtccggt    1200
tatgtaaaca atccggaagc gaccaacgcc ttgattgaca aggatggatg gctacattct    1260
ggagacttag cttactggga cgaagacgaa cacttcttca tagttgaccg cttgaagtct    1320
ttaattaaat acaaaggata tcaggtggcc cccgctgaat tggaatcgat attgttacaa    1380
caccccaaca tcttcgacgc gggcgtgca ggtcttcccg acgatgacgc cggtgaactt    1440
cccgccgccg ttgttgttt ggagcacgga aagacgatga cggaaaaaga gatcgtggat    1500
tacgtcgcca gtcaagtaac aaccgcgaaa aagttgcgcg gaggagttgt gtttgtggac    1560
gaagtaccga aggtcttac cggaaaacgc gacgcaagaa aaatcagaga gatcctcata    1620
aaggccaaga agggcggaaa gtccaaattg                                      1650
```

<210> SEQ ID NO 46
<211> LENGTH: 29
<212> TYPE: DNA
<213> ORGANISM: Artificial Sequence
<220> FEATURE:
<223> OTHER INFORMATION: Synthetic Construct

<400> SEQUENCE: 46

```
gactcatatg gaaaacatgg agaacgatg                                        29
```

<210> SEQ ID NO 47
<211> LENGTH: 25
<212> TYPE: DNA
<213> ORGANISM: Artificial Sequence
<220> FEATURE:
<223> OTHER INFORMATION: Synthetic Construct

<400> SEQUENCE: 47
gacactcgag catcttagca actgg                                          25

<210> SEQ ID NO 48
<211> LENGTH: 1644
<212> TYPE: DNA
<213> ORGANISM: Luciola lateralis

<400> SEQUENCE: 48
atggaaaaca tggagaacga tgaaaatatt gtgtatggtc ctgaaccatt ttaccctatt     60
gaagagggat ctgctggagc acaattgcgc aagtatatgg atcgatatgc aaaacttgga    120
gcaattgctt ttactaacgc acttaccggt gtcgattata cgtacgccga atacttagaa    180
aaatcatgct gtctaggaga ggctttaaag aattatggtt tggttgttga tggaagaatt    240
gcgttatgca gtgaaaactg tgaagaattc tttattcctg tattagccgg tttatttata    300
ggtgtcggcg tggctccaac taatgagatt tacactctac gtgaattggt tcacagttta    360
ggcatctcta agccaacaat tgtatttagt tctaaaaaag gattagataa agttataact    420
gtacaaaaaa cggtaactgc tattaaaacc attgttatat tggacagcaa ggtggattat    480
agaggttatc aatcgatgga caactttatt aaaaaaaaca ctccaccagg tttcaaagga    540
tcaagtttta aaactgtaga agttaaccgc aagaacaag ttgctctcat aatgaactct    600
tcgggttcta ccggtttgcc aaaaggtgtg caacttactc atgaaaatgc agtcactaga    660
ttttctcacg ctagagatcc aatttatgga accaagttt caccaggcac ggctatttta    720
actgtagtac cattccatca tggttttggt atgtttacta ctttaggcta tctaacttgt    780
ggttttcgta ttgtcatgtt aacaaaattt gacgaagaaa cttttctaaa aacactgcaa    840
gattacaaat gttcaagcgt tattcttgta ccgactttgt ttgcaattct taatagaagt    900
gaattactcg ataaatatga tttatcaaat ttagttgaaa ttgcatctgg cggagcacct    960
ttatctaaag aaattggtga agctgttgct agacgtttta atttaccggg tgttcgtcag   1020
ggctatggtt taacagaaac aacctctgca attattatca caccggaagg cgatgataaa   1080
ccaggtgctt ctggcaaagt gtgtgccatta tttaaagcaa aagttatcga tcttgatact   1140
aaaaaaactt gggcccgaa cagacgtgga gaagtttgtg taagggtcc tatgcttatg   1200 aaaggttatg tagataatcc agaagcaaca agagaaatca tagatgaaga aggttggttg   1260
cacacaggag atattgggta ttacgatgaa gaaaaacatt tctttatcgt ggatcgtttg   1320
aagtctttaa tcaaatacaa aggatatcaa gtaccacctg ctgaattaga atctgttctt   1380
ttgcaacatc caaatatttt tgatgccggc gttgctggcg ttccagatcc tatagctggt   1440
gagcttccgg gagctgttgt tgtacttgaa aaggaaaat ctatgactga aaaagaagta   1500
atggattacg ttgcaagtca agtttcaaat gcaaacgtt tgcgtggtgg tgtccgtttt   1560
gtggacgaag tgcctaaagg tcttactggt aaaattgacg gtaaagcaat tagagaaata   1620
ctgaagaaac cagttgctaa gatg                                          1644

<210> SEQ ID NO 49
<211> LENGTH: 22
<212> TYPE: DNA
<213> ORGANISM: Artificial Sequence
<220> FEATURE:
<223> OTHER INFORMATION: Synthetic Construct

<400> SEQUENCE: 49
gttaagccag tttacactcc gc                                             22

<210> SEQ ID NO 50
<211> LENGTH: 34
<212> TYPE: DNA
<213> ORGANISM: Artificial Sequence
<220> FEATURE:
<223> OTHER INFORMATION: Synthetic Construct

<400> SEQUENCE: 50
ggttggttgc acacaggaga tcttgggtat tacg                                 34

<210> SEQ ID NO 51
<211> LENGTH: 24
<212> TYPE: DNA
<213> ORGANISM: Artificial Sequence
<220> FEATURE:
<223> OTHER INFORMATION: Synthetic Construct

<400> SEQUENCE: 51
ctttatcgtg ggtcgtttga agtc                                            24

<210> SEQ ID NO 52
<211> LENGTH: 29
<212> TYPE: DNA
<213> ORGANISM: Artificial Sequence
<220> FEATURE:
<223> OTHER INFORMATION: Synthetic Construct

<400> SEQUENCE: 52
ggtcttactg gtaaaaggga cggtaaagc                                       29

<210> SEQ ID NO 53
<211> LENGTH: 28
<212> TYPE: DNA
<213> ORGANISM: Artificial Sequence
<220> FEATURE:
<223> OTHER INFORMATION: Synthetic Construct

<400> SEQUENCE: 53
gactccatgg aaaacatgga aaacgatg                                        28

<210> SEQ ID NO 54
<211> LENGTH: 1644
<212> TYPE: DNA
<213> ORGANISM: Luciola cruciata

<400> SEQUENCE: 54
atggaaaaca tggaaaacga tgaaaatatt gtagttggac ctaaaccgtt ttaccctatc     60
gaagagggat ctgctggaac acaattacgc aaatacatgg agcgatatgc aaaacttggc    120
gcaattgctt ttacaaatgc agttactggt gttgattatt cttacgccga atacttggag    180
aaatcatgtt gtctaggaaa agctttgcaa aattatggtt tggttgttga tgcagaatt     240 gcgttatgca gtgaaaactg tgaagaattt tttattcctg taatagccgg actgtttata    300
ggtgtaggtg ttgcacccac taatgagatt tacactttac gtgaactggt tcacagttta    360
ggtatctcta aaccaacaat tgtatttagt tctaaaaaag cttagataa agttataaca    420 gtacagaaaa cagtaactac tattaaaacc attgttatac tagatagcaa agttgattat    480
cgaggatatc aatgtctgga caccttata aaaagaaaca ctccaccagg ttttcaagca    540
tccagtttca aaactgtgga agttgaccgc aaagaacaag ttgctcttat aatgaactct    600
tcaggttcta ccggtttgcc aaaaggcgta caacttactc acgaaaatac agtcactaga    660
ttttctcatg ctagagatcc gatttatggt aaccaagttt caccaggcac cgctgtttta    720

```
actgtcgttc cattccatca tggttttggt atgttcacta ctctagggta tttaatttgt    780
ggttttcgtg ttgtaatgtt aacaaaattc gatgaagaaa cattttaaa aactctacaa     840 gattataaat gtacaagtgt tattcttgta ccgaccttgt ttgcaattct caacaaaagt    900
gaattactca ataaatacga tttgtcaaat ttagttgaga ttgcatctgg cggagcacct    960
ttatcaaaag aagttggtga agctgttgct agacgcttta atcttcccgg tgttcgtcaa   1020
ggttatggtt aacagaaac aacatctgcc attattatta caccagaagg tgacgataaa   1080
ccaggagctt ctggaaaagt cgtgccgttg tttaaagcaa aagttattga tcttgatacc   1140
aaaaaatctt taggtcctaa cagacgtgga gaagtttgtg ttaaaggacc tatgcttatg   1200
aaaggttatg taaataatcc agaagcaaca aaagaactta ttgacgaaga aggttggctg   1260
cacaccggag atattggata ttatgatgaa gaaaaacatt tctttattgt cgatcgtttg   1320
aagtctttaa tcaaatacaa aggataccaa gtaccacctg ccgaattaga atccgttctt   1380
ttgcaacatc catctatctt tgatgctggt gttgccggcg ttcctgatcc tgtagctggc   1440
gagcttccag gagccgttgt tgtactggaa agcggaaaaa atatgaccga aaagaagta    1500 atggattacg ttgcaagtca gtttcaaat gcaaaacgtt tgcgtggtgg tgttcgttt    1560 gtggatgaag tacctaaagg tcttactgga aaaattgacg gcagagcaat tagagaaatc   1620
cttaagaaac cagttgctaa gatg                                          1644

<210> SEQ ID NO 55
<211> LENGTH: 26
<212> TYPE: DNA
<213> ORGANISM: Artificial Sequence
<220> FEATURE:
<223> OTHER INFORMATION: Synthetic Construct

<400> SEQUENCE: 55
gcacaccgga gatcttggat attatg                                          26

<210> SEQ ID NO 56
<211> LENGTH: 24
<212> TYPE: DNA
<213> ORGANISM: Artificial Sequence
<220> FEATURE:
<223> OTHER INFORMATION: Synthetic Construct

<400> SEQUENCE: 56
ctttattgtc ggtcgtttga agtc                                            24

<210> SEQ ID NO 57
<211> LENGTH: 29
<212> TYPE: DNA
<213> ORGANISM: Artificial Sequence
<220> FEATURE:
<223> OTHER INFORMATION: Synthetic Construct

<400> SEQUENCE: 57
ggtcttactg gaaaaaggga cggcagagc                                       29
```